US005773236A

United States Patent [19]
Diwu et al.

[11] Patent Number: 5,773,236
[45] Date of Patent: Jun. 30, 1998

[54] ASSAY FOR GLUTATHIANE TRANSFERASE USING POLYHALOARYL-SUBSTITUTED REPORTER MOLECULES

[75] Inventors: Zhenjun Diwu; Richard P. Haugland, both of Eugene, Oreg.

[73] Assignee: Molecule Probes, Inc., Eugene, Oreg.

[21] Appl. No.: 845,301

[22] Filed: Apr. 25, 1997

[51] Int. Cl.⁶ .......................... A61K 38/06; C07D 311/82
[52] U.S. Cl. .......................... 435/15; 530/300; 549/223; 549/228
[58] Field of Search .............................. 435/15; 530/300; 549/223, 228

[56] References Cited

U.S. PATENT DOCUMENTS

| | | | |
|---|---|---|---|
| 4,774,339 | 9/1988 | Haugland et al. | 548/405 |
| 4,810,636 | 3/1989 | Corey | 435/14 |
| 4,812,409 | 3/1989 | Babb et al. | 435/7 |
| 4,945,171 | 7/1990 | Haugland et al. | 549/224 |
| 5,070,012 | 12/1991 | Nolan et al. | 435/6 |
| 5,187,288 | 2/1993 | Kang et al. | 548/110 |
| 5,208,148 | 5/1993 | Haugland et al. | 435/14 |
| 5,227,487 | 7/1993 | Haugland et al. | 546/15 |
| 5,242,805 | 9/1993 | Naleway et al. | 435/18 |
| 5,248,782 | 9/1993 | Haugland et al. | 548/110 |
| 5,274,113 | 12/1993 | Kang et al. | 548/405 |
| 5,362,628 | 11/1994 | Haugland et al. | 435/18 |
| 5,433,896 | 7/1995 | Kang et al. | 252/700 |
| 5,459,268 | 10/1995 | Haugland et al. | 546/37 |
| 5,576,424 | 11/1996 | Mao et al. | 536/17.9 |
| 5,670,644 | 9/1997 | Akhavan-Tafti et al. | 546/103 |

OTHER PUBLICATIONS

Hedley, et al. Cytometry 15, 349 (1994).
Gee, et al. Tet. Lett. 37, 7905 (1996).
Glutathione Conjugation, pp. 357–386, Sies & Ketterer, ed. (1988).
Nakai, et al., J. Biol. Chem. 267, 19503 (1992).

*Primary Examiner*—Gary L. Kunz
*Attorney, Agent, or Firm*—Allegra J. Helfenstein; Anton E. Skaugset

[57] ABSTRACT

The subject invention describes compounds containing a polyhalogenated aryl moiety. The compounds of the invention are particularly useful for the assay of a variety of enzymes, including intracellular enzymes. The subject invention also describes assays for glutathione and/or glutathione transferase enzymes. Selected compounds of the invention are particularly useful for improving the retention of fluorescent products of enzyme metabolism in cells.

86 Claims, 4 Drawing Sheets

ASSAY FOR GLUTATHIANE TRANSFERASE USING POLYHALOARYL-SUBSTITUTED REPORTER MOLECULES

FIELD OF THE INVENTION

The subject invention describes compounds containing a polyhalogenated aryl moiety (PHA). The PHA derivatives of the invention are particularly useful for the assay of a variety of enzymes, including intracellular enzymes. The subject invention also describes assays for glutathione and/or glutathione transferase enzymes. Selected compounds are particularly useful for improving the retention of fluorescent products of enzyme metabolism in cells.

BACKGROUND OF THE INVENTION

The presence and activity of enzymes can be used to determine the health and metabolic state of a cell, or to distinguish one cell from another. Enzyme conjugates and enzyme fusion proteins are common bioanalytical tools useful in histochemistry, molecular biology and other fields. Enzymes are useful reporters of gene expression, including transfected foreign genes.

Synthetic substrates are routinely used to detect or assay isolated enzymes, enzymes in bodily fluids and in cell lysates. Synthetic probes for assessing enzyme activity in normal and metabolically compromised single cells are important for the evaluation of drugs, diseases, and other conditions that affect enzyme activity. Synthetic substrates can also be used to detect the presence and activity of enzymes that are present as a result of bacterial, viral or other biological contamination. Substrates that yield a detectable optical property are particularly important. Among these substrates, fluorescent or fluorogenic probes that yield fluorescent reporter products are preferred for the most sensitive measurements, particularly in single cells.

Assays for enzymatic activity in single living cells have been complicated by the difficulty in getting the substrate to the enzyme and/or the difficulty of retaining the (generally fluorescent) reporter product in the cell. A number of mechanisms have been described for loading substrates and retaining the metabolic products of enzymes in cells. Some mechanisms require exposure of cells to abnormal conditions, e.g. hypoosmotic shock and/or low temperatures described in U.S. Pat. No. 5,070,012 (incorporated by reference). Derivatives of fluorescein and resorufin described in U.S. Pat. No. 5,208,148 and U.S. Pat. No. 5,242,805 (both incorporated by reference) utilize a lipophilic residue such as a fatty acid residue to enhance cell loading and retention, but their products are generally not well retained following cell fixation with aldehyde-based fixatives. Haloalkyl-substituted substrates (U.S. Pat. No. 5,362,628 and copending application Ser. No. 08/336,285, both incorporated by reference) and similar molecules targeted at mitochondria (U.S. Pat. No. 5,459,268 and copending application Ser. No. 08/383,298, both incorporated by reference) are retained in fixed cells, but we have shown that the haloalkyl group of these compounds makes these compounds reactive with thiols other than glutathione, where they may inhibit intracellular thiol-dependent enzymes. Furthermore, their synthesis can be time-consuming and expensive.

The compounds of the invention all contain a polyhalogenated aryl (PHA) substituent of defined structure that both enhance the penetration of the substrate through membranes of live cells and improve the retention of reporter products in the cells, including cells fixed with aldehyde-based fixatives, relative to the same substrate lacking the PHA moiety. The PHA derivatives have little if any effect on the cell's viability or other metabolic properties. The PHA moiety, and in particular the fluorine-containing PHA moiety, can be incorporated in a wide variety of low molecular weight molecules, including dyes that are commonly used for the preparation of synthetic substrates, and to thus impart the favorable characteristics of improving cell uptake and retention of products. Surprisingly, the addition of the PHA substituent also appears to increase the aqueous solubility of the substrate, relative to the same substrate without the PHA moiety. Substrates described in the invention that combine the PHA substituent with a chromogenic or fluorogenic substrate for an enzyme other than a glutathione transferase such as a glycosidase, a phosphatase or a peroxidase provide a means to detect the activity of these enzymes both in vivo or in vitro, including on membrane blots.

Although all PHA derivatives are retained in cells, fluorine-containing PHA substrates derived from chromophores or fluorophores are preferred both for ease of analysis and quantitation. Certain fluorine-containing PHA derivatives of the invention also form thioether adducts of glutathione (GSH), typically catalyzed by a glutathione transferase (GST). GST enzymes and GSH are ubiquitous cellular components with important roles in cell protection and disease resistance, including detoxification of xenobiotics through conjugation to GSH and maintenance of the cell's oxidation-reduction (redox) state. The family of GST enzymes comprises several isozymes that are related in function, if not in sequence, but which vary in their response to various agents.

Attempts to assay glutathione content in vivo (i.e. in live cells) and in vitro (i.e. in cell extracts or cell-free solution) have been disappointing; the reagents have lacked specificity for glutathione, resulting in high backgrounds, false results or both, see, e.g. Hedley, et al., Cytometry 15, 349 (1994). Certain fluorinated aryl derivatives, such as 1-fluoro-2,4-dinitrobenzene (FDNB, Sanger's reagent), 4-fluoro-7-nitrobenz-2-oxa-1,3-diazole (NBD fluoride) and certain polyfluorinated derivatives described in copending application Ser. No. 08/631,202, filed Apr. 12, 1996 by Gee et al. (incorporated by reference) and in Gee et al. (TET. LETT. 37, 7905 (1996)) have been shown to react with glutathione, but they generally contain strongly electron withdrawing groups that result in spontaneous reaction of the reagent with thiols other than glutathione, including protein thiols. Two colorimetric reagents that contain a haloaryl moiety and have been found to react specifically with GSH in the presence of GST enzymes, 1-Chloro-2,4-dinitrobenzene (CDNB) and tetrabromophenolsulfonephthalein (BSP) (see, e.g. GLUTATHIONE CONJUGATION pp357–386 (Sies & Ketterer, ed. 1988)) differ in structure from the reagents used to practice the invention in that the colorimetric reagents do not contain a polyfluorinated aryl that is required for GSH specificity in this invention.

The reaction of specific fluorine-containing PHA derivatives with GSH occurs both in vivo and in vitro, but requires a particular minimum number and substitution pattern of fluorine atoms and other substituents. The novel GST-mediated reaction of specific fluorine-containing PHA derivatives of this invention is broadly applicable to the qualitative or quantitative assay of either glutathione or GST enzymes, particularly if the assay methods permit separation of the glutathione adduct from the unconjugated substrate. In contrast to common colorimetric reagents for GSH described above, the compounds of the invention are also suitable for modification to detect a variety of hydrolytic enzymes.

Trace A: A pure sample of 5-(pentafluorobenzoylamino) fluorescein (Compound 1).

Trace B: A mixture of Compound 1 and its glutathione adduct, 5-(4'-(S-glutathionyl))-(2',3',5',6'-tetrafluorobenzoylamino)fluorescein (Compound 45).

Trace C: Cell extracts from cells that have been incubated with 5-(pentafluorobenzoylamino)fluorescein diacetate (Compound 4).

The presence of both Compound 1 and Compound 45 in the cell extract verifies that, in vivo, Compound 4 is hydrolyzed and conjugated to glutathione (as described in Example 66).

Figure 2:
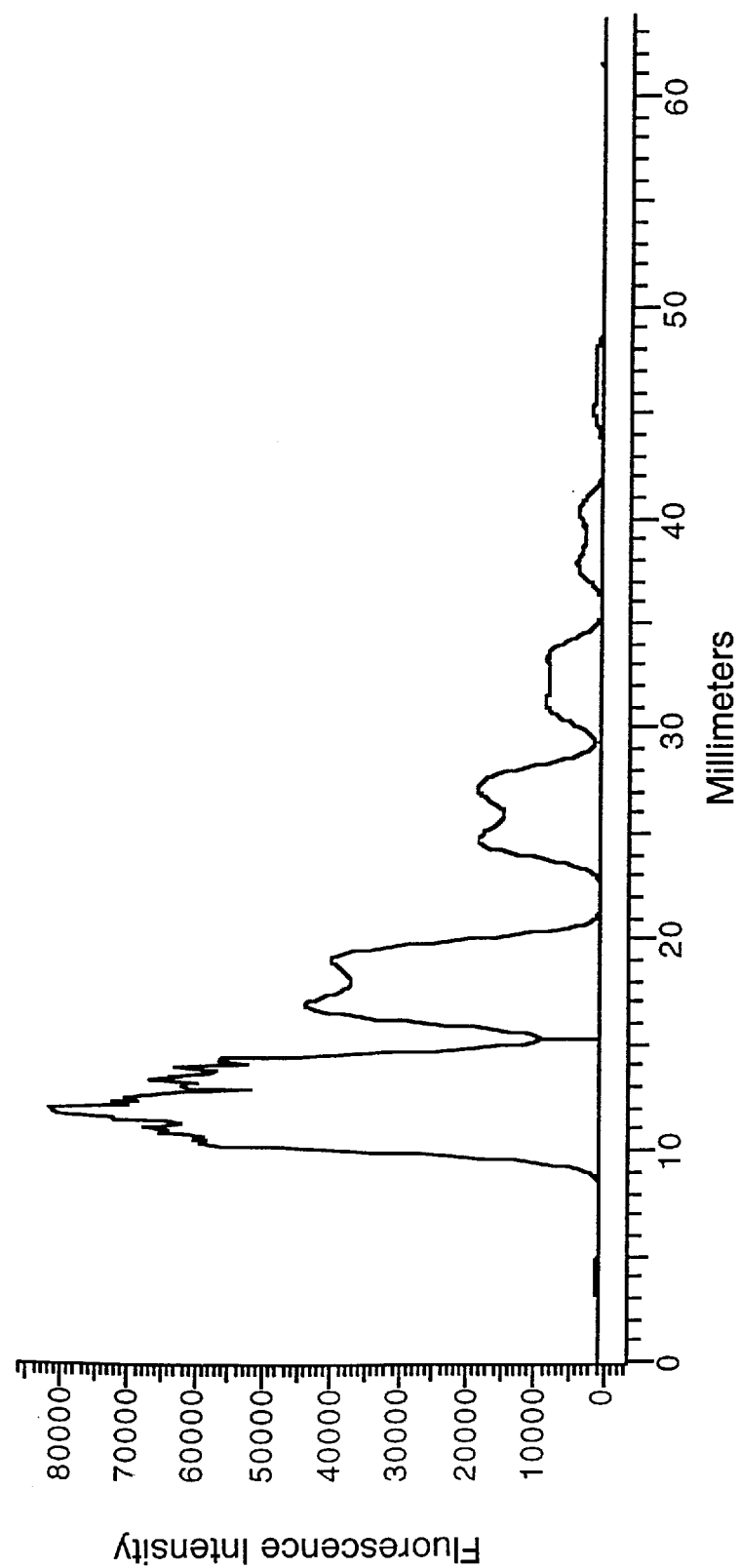

FIG. 2: A fluorescence intensity scan of a TLC plate quantifying the amounts of the GST-catalyzed reaction product of Compound 1 with intracellular GSH (as described in Example 48). The scan is recorded as described in Example 53.

Figure 3:
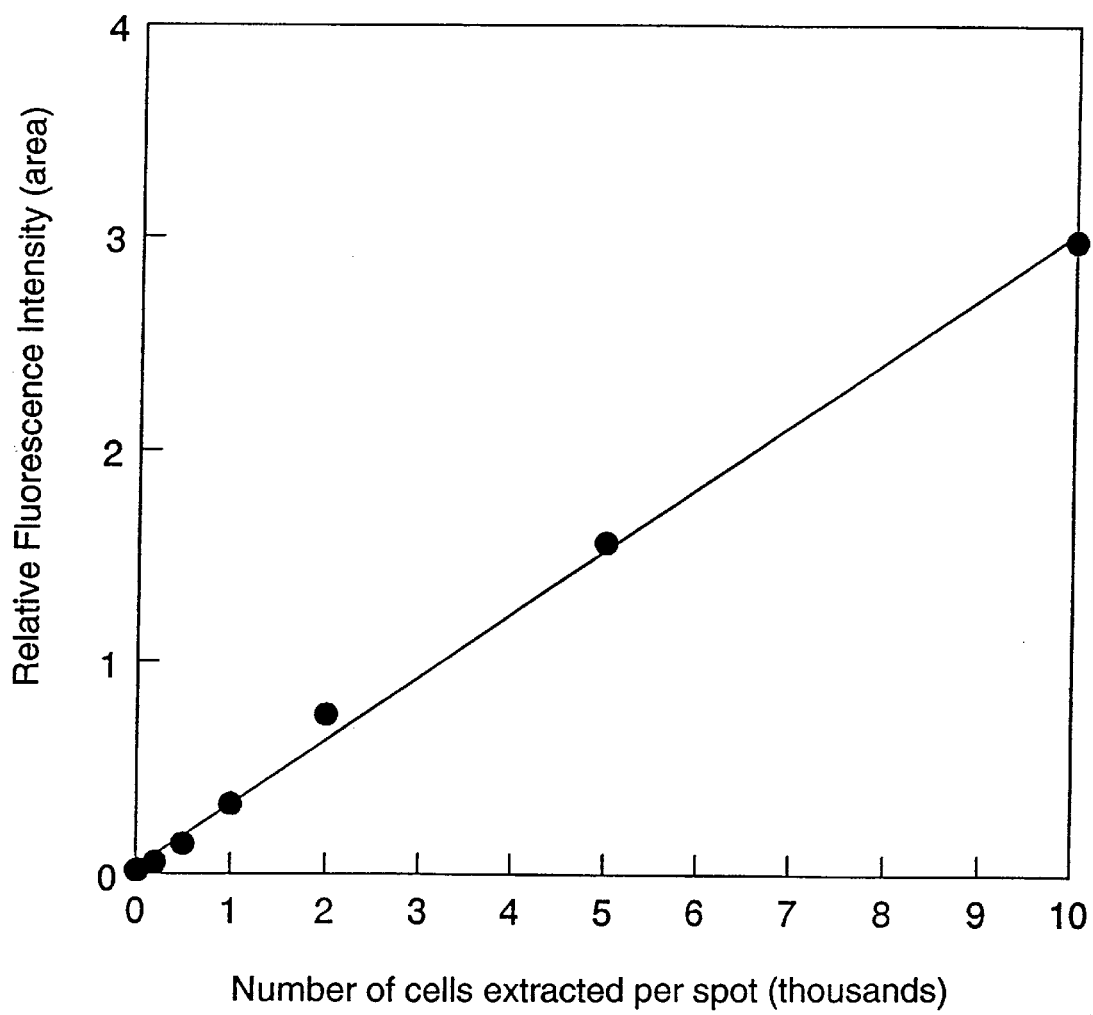

FIG. 3: Quantitation of intracellular glutathione by plotting the fluorescence intensity of the Compound 1-GSH adduct versus the number of cells, as described in Example 56.

Figure 4:
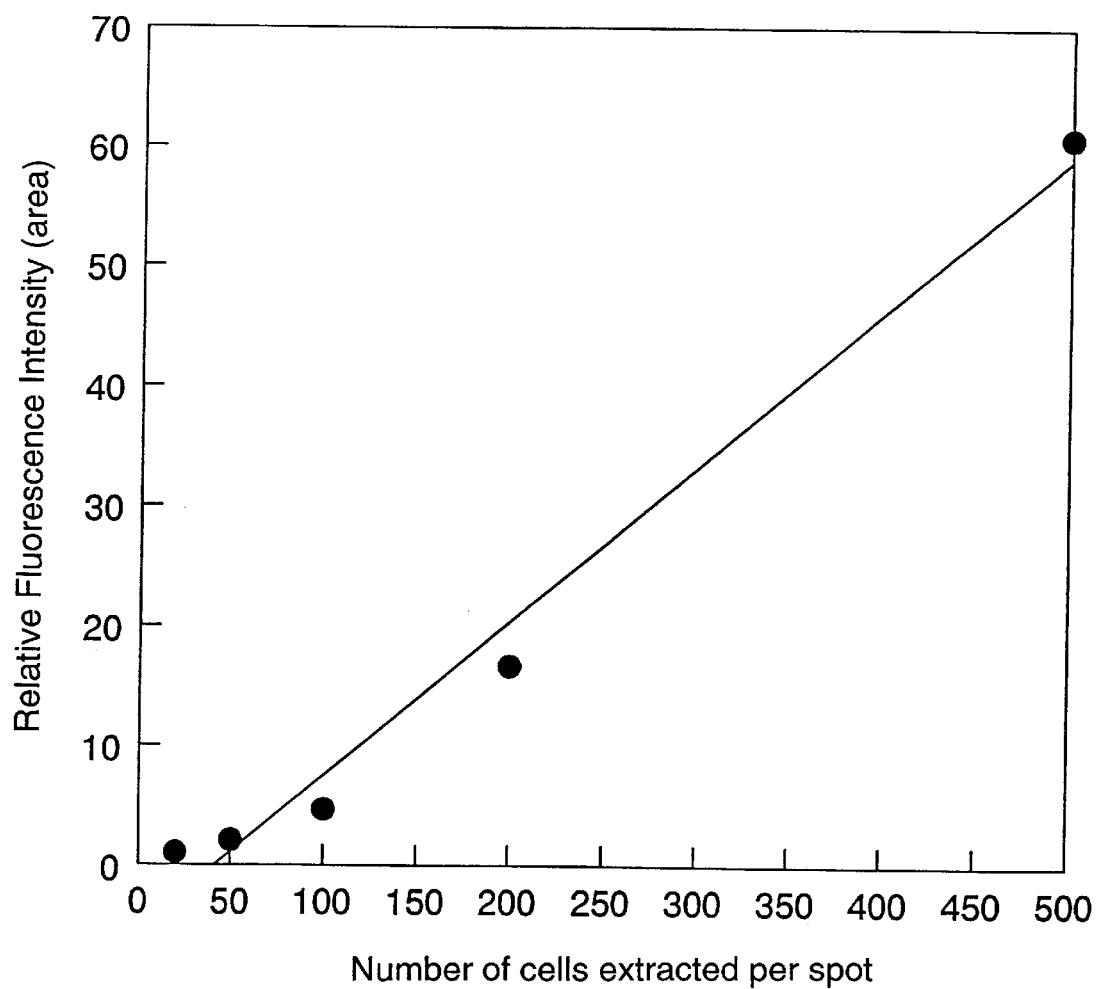

FIG. 4: Quantitation of intracellular glutathione transferase activity by plotting the fluorescence intensity of the Compound 1-GSH adduct versus the number of cells, as described in Example 56.

SUMMARY OF THE INVENTION AND DESCRIPTION OF PREFERRED EMBODIMENTS

This invention describes compounds containing a polyhalogenated aryl moiety (PHA). The compounds of the invention are particularly useful as substrates for enzyme systems. In one embodiment of the invention, the compounds of the invention are useful for detecting the tripeptide glutathione in the presence of a glutathione transferase. In another embodiment, the compounds of the invention are useful for detecting the presence of a glutathione transferase in the presence of glutathione. In yet another embodiment, selected fluorogenic enzyme substrates that are additionally substituted by a PHA are useful for analyzing enzyme activity, both in vivo and in vitro.

The compounds of the invention have the general formula:

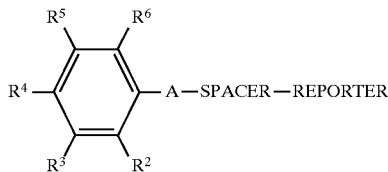

where the aryl substituents $R^2$, $R^3$, $R^4$, $R^5$ and $R^6$ are independently H, F, Cl, Br, $C_1$–$C_6$ alkyl, or $C_1$–$C_6$ alkoxy, provided that at least three of $R^2$, $R^3$, $R^4$, $R^5$ and $R^6$ are halogen (F, Cl, Br). The $R^2$ substituent is additionally permitted to be $SO_3R^7$, $(C=O)OR^7$, or $(C=O)NR^8R^9$, where $R^7$ is H or a suitable salt or counterion (yielding a sulfonic acid, carboxylic acid, or their respective salts), or $R^7$ is a $C_1$–$C_6$ alkyl (yielding a sulfonate ester or carboxylate ester), and $R^8$ and $R^9$ are independently H or a $C_1$–$C_6$ alkyl (yielding a carboxamide).

The A moiety is either a single covalent bond, or A is an electron-withdrawing linking group that permits facile attachment of the PHA moiety to SPACER-REPORTER. Preferred A moieties —(C=O)—, —(C=O)—O—, —(C=O)—$NR^{10}$, —$NR^{10}$—(C=O)—, —(C=$NR^{10}$)—, —CH=N—, —$SO_2$—, —$SO_2$—O—, —$SO_2$—$NR^{10}$—, or —$NR^{10}$—$SO_2$—, where $R^{10}$ is H or $C_1$–$C_6$ alkyl. Most preferably, A is —(C=O)—$NR^{10}$ or —$SO_2$—$NR^{10}$—.

Alternatively, $R^2$ taken in combination with the A moiety forms a 5-membered cyclic imide, so that the PHA moiety is a phthalimide, and the compounds of the invention have the general formula:

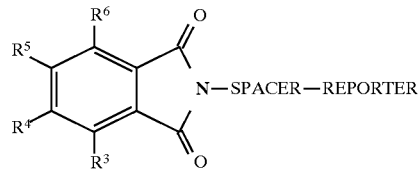

Alternatively, $R^2$ taken in combination with the A moiety forms a 6-membered cyclic hydrazide, so that the PHA moiety is a phthalhydrazide, and the compounds of the invention have the general formula:

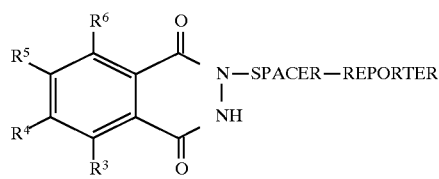

Typically the combination of the PHA moiety and the A moiety is a pentafluorobenzoyl, pentachlorobenzoyl, pentafluorobenzenesulfonyl, pentachlorobenzenesulfonyl, tetrafluorophthalimidyl, or tetrachlorophthalimidyl substituent.

In one embodiment of the invention, the PHA moiety is polyhalogenated, such that at least three of $R^2$, $R^3$, $R^4$, $R^5$ and $R^6$ are independently F, Cl or Br. Preferably at least three of $R^2$, $R^3$, $R^4$, $R^5$ and $R^6$ are F or Cl, more preferably F. Where the compounds of the invention comprise a PHA substituted by at least three halogens, the compounds and their metabolic products are typically well-retained in cells and other lipophilic environments.

In another embodiment of the invention, the PHA moiety is polyfluorinated, such that $R^4$ is F and at least two of $R^3$, $R^5$ and $R^6$ are F, and the A moiety is required to be an electron-withdrawing linking group. Preferably, $R^4$ is F and at least three of $R^2$, $R^3$, $R^5$, and $R^6$ are F, and most preferably each of $R^2$, $R^3$, $R^4$, $R^5$, and $R^6$ are F. Where the $R^2$ substituent on the polyfluoroaryl moiety is a moderately electron-withdrawing group, enzyme-catalyzed substitution of glutathione at the $R^5$ position is possible, provided that $R^5$ is initially fluorine and that at least two of $R^3$, $R^4$ and $R^6$ are also fluorine. Where the compounds of the invention comprise a polyfluorinated aryl as described herein, the compounds of the invention are selective for glutathione, typically requiring a GST enzyme to catalyze the displacement of the fluorine at $R^4$ (or $R^5$) by the glutathione thiolate, yielding a glutathione adduct. The selectivity for GSH is apparently essentially independent of the specific character of the elements SPACER, REPORTER or BLOCK (Example 1). Fluorination at $R^4$, however, appears to be essential, and at least two of $R^3$, $R^5$ and $R^6$ must also be fluorinated for the compound to possess specificity as a substrate for GST. Except under conditions of unusually high thiol concentrations, high temperatures, extended reaction periods and/or the addition of high concentrations of organic solvents, these polyfluorinated aryl-containing compounds do not appear to react with glutathione or other thiols in the absence of GST enzymes.

The substituents SPACER and REPORTER, while having little if any effect on the selectivity of the fluorinated PHA substrates, may be selected to provide greater ease of detection of the substrate and its glutathione adduct, alter the polarity or solubility properties of the reagent, facilitate the synthesis of the desired substrate from commercially available starting materials (in the case of most SPACER moieties), or impart the unique properties of the fluorine-containing PHA group on a substrate for a second enzyme, which utility is particularly important for cellular applications of the PHA-substituted probes and substrates (where REPORTER comprises a blocked dye).

The covalent linkage SPACER is a single covalent bond (provided that A is not simultaneously a single covalent bond), or SPACER is a covalent linkage having 1–24 nonhydrogen atoms selected from the group consisting of C, N, O and S. SPACER is composed of any combination of single, double, triple or aromatic carbon-carbon bonds, carbon-nitrogen bonds, nitrogen-nitrogen bonds, carbon-oxygen bonds and carbon-sulfur bonds. In one embodiment, SPACER is a single covalent bond. In another embodiment, SPACER has the formula —$(CH_2)_n$—NH—(C=O)— or —$(CH_2)_n$—(C=O)—NH—, where n=1–6. In yet another embodiment, SPACER is an arylene, that is, SPACER incorporates a bridging aromatic group. Where SPACER is an arylene, it is preferably phenylene (—$C_6H_4$—) or a heteroarylene of the formula

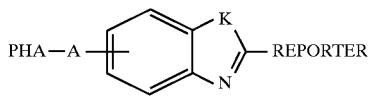

wherein K is O, S or $NR^{13}$, where $R^{13}$ is H or $C_1$–$C_6$ alkyl.

The REPORTER moiety is H or any organic residue that has a definite molecular weight less than 2000 daltons, and is detectable either by observation or instrumentally. REPORTER may be detectable by its presence. Typically REPORTER is detectable by the presence of or a change in, color, fluorescence, reflectance, chemiluminescence, light polarization, light scattering, precipitation, x-ray scattering, electron spin resonance, or the deposition of an electron-rich substrate for visualization by electron microscopy. Preferably, REPORTER is detectable by its optical properties. Typically the detectable response is the presence of or a change in fluorescence, such as intensity, excitation or emission wavelength distribution of fluorescence, fluorescence lifetime, fluorescence polarization, or a combination thereof.

Where the PHA moiety is polyfluorinated and can serve as a substrate for glutathione transferase, REPORTER is any grouping of molecules that facilitates differentiation between the substrate and the glutathione adduct resulting from the action of glutathione transferase. Where differentiation can be accomplished by a highly sensitive analytical technique such as mass spectroscopy, REPORTER can simply be H, butyl, or another simple organic residue. Where the analytical technique relies on chromatography or electrophoresis, REPORTER is a detectable organic residue of less than 2000 daltons. Preferably, each glutathione transferase substrate in the assay solution will have the same REPORTER moiety, have the same molecular weight, chemical formula and isomeric configuration, to minimize the number of discrete species detected during subsequent analytical methods.

In one embodiment, REPORTER is selected so as to be readily detectable using conventional analytical instrumentation, such as where REPORTER is a radioactive element, a spin label, or a dye moiety, or where REPORTER contains a moiety that is readily identifiable by its magnetic resonance spectrum, such as a methyl, a tert-butyl, an aryl or a fluorine atom.

Where REPORTER is a dye moiety, REPORTER can be any of a variety of chromophores, chromogenic substrates (chromophore precursors), fluorophores, fluorogenic substrates (fluorophore precursors), phosphorescent moieties, or chemiluminescent precursors. By chemiluminescent precursor is meant a compound that on treatment with an enzyme or chemical reagent produces chemiluminescence. Examples of chemiluminescent precursors include adamantane oxetanes, lucigenins, acridinium esters, luminols and isoluminols.

Where REPORTER is selected to be a chromophore or fluorophore, REPORTER is preferably a moiety that possesses an absorption peak beyond 210 nm, preferably beyond 300 nm and more preferably beyond 350 nm. If REPORTER is a fluorophore, it preferably has a visible emission peak beyond 420 nm. Typically, where REPORTER is a fluorophore, REPORTER is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a porphyrin, a salicylate, an anthranilate, an azulene, a perylene, a pyridine, a quinoline, a coumarin (including hydroxycoumarins and aminocoumarins and fluorinated and sulfonated derivatives thereof as described in copending application Ser. Nos. 08/749,753 and 08/749,684, both filed Nov. 15, 1996 and incorporated by reference), a 4-bora-3a,4a-diaza-s-indacene (e.g. U.S. Pat. Nos. 4,774, 339 to Haugland, et al. (1988); 5,187,288 to Kang, et al. (1993); 5,248,782 to Haugland, et al. (1993); 5,274,113 to Kang, et al. (1993); and 5,433,896 to Kang, et al. (1995), all incorporated by reference), a xanthene, an oxazine or a benzoxazine, a carbazine (U.S. Pat. No. 4,810,636 to Corey (1989), incorporated by reference), or a phenalenone or benzphenalenone (U.S. Pat. No. 4,812,409 Babb et al. (1989), incorporated by reference), or a lanthanide chelate.

Preferably, where REPORTER is a fluorophore, REPORTER is a carbazine, an oxazine, a coumarin, a xanthene, a naphthalene, a phenalenone, or a 4-bora-3a,4a-diaza-s-indacene.

Where REPORTER is a xanthene, REPORTER is optionally a fluorescein, a rhodol (U.S. Pat. No. 5,227,487 to Haugland, et al. (1993), incorporated by reference), or a rhodamine. As used herein, fluorescein includes benzo- or dibenzofluoresceins, seminaphthofluoresceins, naphthofluoresceins or seminaphthorhodafluors (U.S. Pat. No. 4,945, 171 to Haugland, et al. (1990), incorporated by reference). As used herein, oxazines include resorufins, aminooxazineones and diaminooxazines.

In another embodiment, the xanthene is a dihydroxanthene that is a substrate for an oxidative enzyme or other reactive oxidizing agent, particularly a peroxidase enzyme, including the action of horseradish peroxidase in combination with peroxides or solely by nitric oxide. A wide variety of oxidizing agents mediate the oxidation of the dihydroxanthenes, including molecular oxygen in the presence or absence of a catalyst, nitric oxide, peroxynitrite, dichromate, triphenylcarbenium and chloranil.

Preferably, REPORTER is a coumarin, a 4-bora-3a,4a-diaza-s-indacene, a fluorescein, a rhodol, a rhodamine or a resorufin.

In one embodiment, REPORTER is a chromophore, a fluorophore, or a chemiluminescent precursor. In another embodiment, REPORTER has the formula DYE-(BLOCK)$_a$. In this embodiment, DYE is a chromophore, a fluorophore, or a chemiluminescent precursor, and BLOCK is a monovalent moiety selected to be removable by action of a selected enzyme. In particular, BLOCK is selected such that while BLOCK is bound to DYE, DYE has spectral properties different from those of the free chromophore, fluorophore or chemiluminescent precursor, such as detectably different wavelengths of maximal absorbance, restoration of fluorescence, or generation of luminescence. Where REPORTER is a DYE-(BLOCK)$_a$, and DYE is a fluorophore, REPORTER is a fluorogenic enzyme substrate. In one embodiment, action of the selected enzyme in removing BLOCK results in a shift in the absorbance of the resultant product to longer wavelengths that are not absorbed or are minimally absorbed before the removal of BLOCK. BLOCK is typically selected to be removable only by the action of a specific enzyme or chemical substance predetermined to be of analytical interest. Preferably BLOCK is removed only when the selected enzyme is present. When DYE is no longer bound to BLOCK by a DYE-BLOCK bond, as when that bond has been cleaved by the selected enzyme, the spectral properties of the fluorophore are restored. Selected fluorophores, such as xanthenes may be blocked at one or two positions, so that a=1 or 2. For those embodiments wherein FLUOR is substituted by multiple BLOCK moieties, each BLOCK may be the same or different.

In one embodiment BLOCK is a monovalent moiety formally derived by removal of a hydroxy group from a phosphate, a sulfate, or a biologically compatible salt thereof. Phosphate and sulfate, as used herein, optionally include phosphate esters or diesters (such as phosphorylcholine or nucleotide or oligonucleotide phosphates) or sulfonate esters. In this case a biologically compatible salt is a cation that is not toxic as used, and does not have a substantially deleterious effect on biomolecules. Examples of biologically compatible cationic salts include, among others, sodium, potassium, ammonium, and alkylammonium.

In another embodiment, BLOCK is a monovalent moiety formally derived by removal of a hydroxy group from a carboxy group of a $C_1$–$C_{18}$ aliphatic acid, an aromatic acid (such as a p-guanidinobenzoic acid), an amino acid, a protected amino acid, or a peptide. Compounds in which BLOCK is derived from a carboxylic acid are typically useful as esterase substrates. Conjugates of amino-substituted fluorophores of the invention, including of aminocoumarin, rhodol and rhodamine dyes that are amino acid or peptide amides are typically useful as peptidase substrates. Preferred substrates are those for aminopeptidases and dipeptidyl peptidases. Particularly preferred are substrates for dipeptidyl peptidases I, II and IV, calpain, elastase, trypsin, chymotrypsin, granzyme A, thrombin, cathepsins, urokinase, kallikrein, human adenovirus proteinase, plasminogen activator, interleukin converting enzyme (ICE), amyloid A4-generating enzyme, follipsin, leucine aminopeptidase and arginine aminopeptidase.

In yet another embodiment, BLOCK is a monovalent moiety formally derived by removal of a hydroxy group from a $C_1$–$C_{12}$ aliphatic or aryl-aliphatic alcohol, or from a mono-, or a polysaccharide.

Compounds wherein BLOCK is an aliphatic or aryl-aliphatic ether are substrates for enzymes such as the microsomal dealkylases (e.g. cytochrome P450). Primary examples include 7-alkoxycoumarins and ethers of resorufins (Nakai, et al., J. BIOL. CHEM. 267, 19503 (1992), incorporated by reference). Because the microsomal dealkylase enzymes typically have low turnover rates in cells, it is difficult to detect the fluorescent product in single cells unless a substrate that is well-retained in cells is used. Glycosidase substrates are particularly useful for detection of metabolic deficiency in cells that result from genetic diseases, detection of gene markers, detection of contamination of samples by bacteria and other applications. Where BLOCK is derived from a mono- or polysaccharide, the carbohydrate portion is linked through its anomeric carbon to a phenolic oxygen atom on DYE via either an α- or β-ether linkage. Typically the carbohydrate is a monosaccharide that is a pentose or hexose, (e.g. a glucose, galactose, glucuronic acid, glucosamine, galactosamine, mannose, xylose, ribose or fucose) or a more complex monosaccharide such as neuraminic (sialic) acid, or is a disaccharide (e.g. cellobiose, lactose or sucrose).

Typically, DYE-BLOCK bond is an ether or ester bond (e.g,. for hydroxycoumarin, fluorescein, rhodol or resorufin derivatives), or DYE-BLOCK is an amide bond (e.g. for aminocoumarin, rhodamine or rhodol derivatives).

Representative enzymes for which substrates of the invention that contain an element BLOCK are useful include those in Table 1.

TABLE 1

Representative Enzymes

| E.C. NO. | ENZYME | TARGET GROUP |
|---|---|---|
| 3.2.1.20 | α-Glucosidase | α-D-Glucose |
| 3.2.1.21 | β-Glucosidase | β-D-Glucose |
| 3.2.1.22 | α-Galactosidase | α-D-Galactose |
| 3.2.1.23 | β-Galactosidase | β-D-Galactose |
| 3.2.1.24 | α-Mannosidase | α-D-Mannose |
| 3.2.1.25 | β-Mannosidase | β-D-Mannose |
| 3.2.1.30 | N-Acetyl-β-D-Glucosaminidase | β-D-N-Acetyl-Glucosamine |
| 3.2.1.31 | β-Glucuronidase | β-D-Glucuronic Acid |
| 3.2.1.38 | β-D-Fucosidase | β-D-Fucose |
| 3.2.1.51 | α-L-Fucosidase | α-L-Fucose |
| 3.2.1-- | β-L-Fucosidase | β-L-Fucose |
| 3.2.1.76 | L-Iduronidase | α-L-Iduronic Acid |
| 3.2.1.4 | Cellulase | β-D-Cellobiose |
| 3.2.1-- | α-Arabinopyranosidase | α-L-Arabinopyranose |
| 3.2.1.37 | β-Xylosidase | β-D-Xylose |

TABLE 1-continued

Representative Enzymes

| E.C. NO. | ENZYME | TARGET GROUP |
|---|---|---|
| 3.2.1.18 | α-N-Acetyl-neuraminidase | α-D-N-Acetyl-neuraminic acid (Sialic acid) |
| 3.1.1-- | Guanidinobenzoatase | aryl esters of p-guanidinobenzoate |
| 3.1.3.1 | Alkaline phosphatase | aryl or alkyl phosphate monoesters |
| 3.1.3.2 | Acid phosphatase | aryl or alkyl phosphate monoesters |
| 3.1.6.1 | Aryl sulfatase | aryl sulfate monoesters |
| 3.4.11.1 | Leucine amino peptidase | leucine residues at α-carboxyl |

The preferred PHA derivatives of the invention for detecting the activity of an enzyme that is not glutathione transferase have a REPORTER that is DYE-(BLOCK)$_a$ and DYE is a coumarin, a xanthene or an oxazine (particularly a resorufin).

When REPORTER incorporates a coumarin, the compound typically has the structure

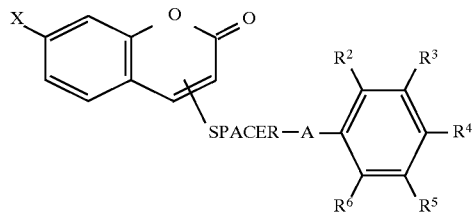

where the X substituent on the coumarin is BLOCK—O—, BLOCK—NR$^{11}$—, HO— or R$^{11}$R$^{12}$N—, where R$^{11}$ and R$^{12}$ are independently H or C$_1$–C$_6$ alkyl. Alternatively, R$^{11}$ and R$^{12}$ taken in combination form a pyrrolidine, a piperidine, a morpholine or a piperazine. In another embodiment, one or both of R$^{11}$ and R$^{12}$ in combination with the 6- and 8-positions on the coumarin form a 5- or 6-membered saturated or unsaturated ring that is optionally substituted one or more times by methyl. The coumarin fluorophore itself is allowed to be additionally substituted by H, halogen, sulfo, C$_1$–C$_6$ alkyl, C$_1$–C$_6$ perfluoroalkyl, C$_1$–C$_6$ alkoxy, cyano or halomethyl in any combination.

Preferably, X has the formula BLOCK—O— and BLOCK is derived by removing a hydroxy group from a from a C$_1$–C$_6$ alcohol or from a mono- or polysaccharide, or X has the formula BLOCK—NR$^{11}$—, and BLOCK is derived by removal of a hydroxy group from a carboxylic acid of an amino acid or peptide.

For ease of synthesis from readily available starting materials, the moiety PHA-A-SPACER is typically conjugated to the coumarin at the 3- or 4-position on the coumarin pyrone ring. Preferred A moieties in this embodiment are —(C=O)—NH—, —NH—(C=O)— and —SO$_2$NH—. Preferred SPACER moieties in this embodiment are —(CH$_2$)$_n$—NH—(C=O)—, —(CH$_2$)$_n$—(C=O)—NH—, —(CH$_2$)$_n$—HNO$_2$S— or —(CH$_2$)$_n$—NH—(C=S)—NH—, —(CH$_2$)$_n$—NH—(C=O)—(CH$_2$)$_m$— (where m and n are independently 1 to 6), or an arylene, as previously defined.

In one embodiment, REPORTER incorporates a xanthene, and the compound has the structure:

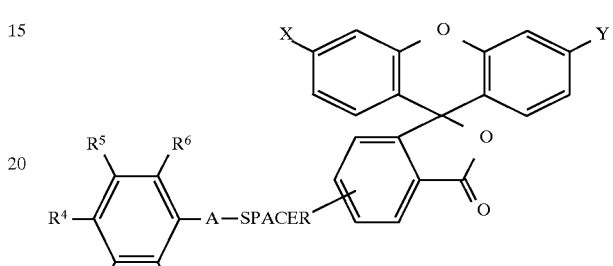

or the compound has the structure:

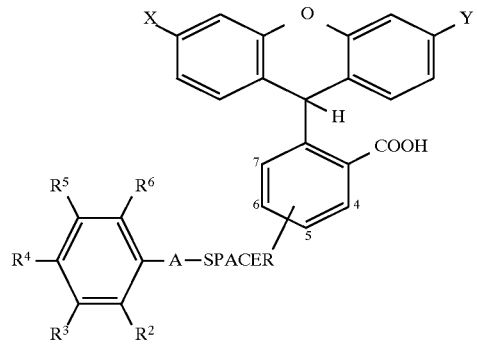

wherein the X and Y substituents on the xanthene are independently BLOCK—O—, BLOCK—NR$^{11}$—, HO— or R$^{11}$R$^{12}$N—, where R$^{11}$ and R$^{12}$ are defined as above, including one or both of R$^{11}$ and R$^{12}$ in combination with a xanthene position ortho to X or Y forming a 5- or 6-membered saturated or unsaturated ring that is optionally substituted one or more times by methyl. The xanthene is optionally substituted by H, halogen, C$_1$–C$_6$ alkyl or C$_1$–C$_6$ alkoxy in any combination.

Typically X and Y are both BLOCK—NR$^{11}$—, and BLOCK is derived by removal of a hydroxy group from a carboxylic acid of an amino acid or peptide; or X and Y are both BLOCK—O—, and BLOCK is derived by removal of a hydroxy from a glycoside, a carboxylic acid, a phosphate, or a sulfate. Preferably, in this embodiment of the invention, X and Y are both BLOCK—O— and each BLOCK is derived by removal of a hydroxy group from α-D-galactose, α-D-glucose, α-D-glucuronic acid, β-D-galactose, β-D-glucose or β-D-glucuronic acid; or each BLOCK is acetate.

Preferably A is —NH—(C=O)—, —(C=O)—NH— or —SO$_2$NH—. SPACER is preferably a single chemical bond or is —(CH$_2$)$_n$—NH—(C=O)— or —(CH$_2$)$_n$—(C=O)—NH—, or is —(CH$_2$)$_n$—NH—(C=S)—, where n=1–6.

If the xanthene is a fluorescein, then X and Y are independently BLOCK—O— or HO—. If the dye is a rhodol then one of X and Y is a BLOCK—$NR^{11}$— or $NR^{11}R^{12}$— while the other is BLOCK—O— or HO—. If the xanthene is a rhodamine, then both X and Y are BLOCK—$NR^{11}$— or $NR^{11}R^{12}$—.

The xanthene is preferably a fluorescein, a rhodol or a rhodamine, although analogous blocked xanthenes may be prepared using known precursors and methods known in the art to prepare benzofluoresceins, dibenzofluoresceins, semi-naphthofluoresceins or seminaphthorhodafluors. When the molecule contains two elements BLOCK, the elements BLOCK are the same or different, typically the same. Except in the case where the xanthene has two elements BLOCK, the compound exists in equilibrium with a colored form in which the lactone ring is open that is a carboxylic acid or salt of a carboxylic acid with a cation. In this form of a xanthene of the invention PHA-A-SPACER is covalently bonded to the "bottom ring" of the xanthene dye, preferably at either the 5- or 6-position of the above structure.

In another embodiment, the xanthene has the formula

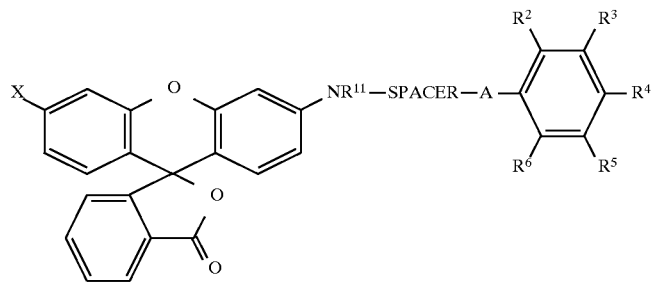

or the formula

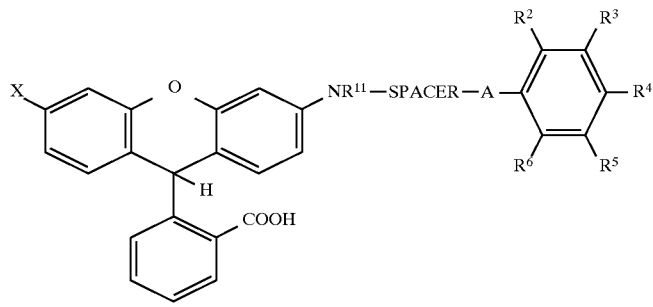

wherein

X and $R^{11}$ are defined as described above and the xanthene fluorophore is optionally substituted by H, halogen, $C_1$–$C_6$ alkyl or $C_1$–$C_6$ alkoxy, in any combination.

In this embodiment X is typically BLOCK—$NR^{11}$—, and BLOCK is derived by removal of a hydroxy group from a carboxylic acid of an amino acid or peptide; or X is BLOCK—O—, and BLOCK is derived by removal of a hydroxy from a glycoside, a carboxylic acid, a phosphate, or a sulfate.

In another embodiment, REPORTER incorporates a resorufin and has the structure:

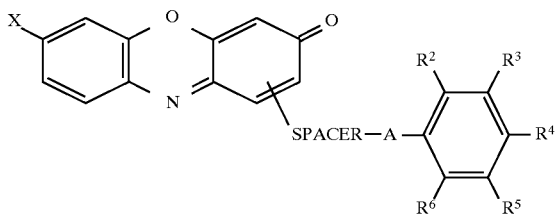

wherein X is BLOCK—O—, or HO—; and resorufin fluorophore is further substituted by H, halogen, $C_1$–$C_6$ alkyl or $C_1$–$C_6$ alkoxy, in any combination.

In this embodiment, BLOCK is typically derived by removal of a hydroxy from a glycoside, a carboxylic acid, a phosphate, or a sulfate.

In all embodiments except where REPORTER is a coumarin, a resorufin or a 4-bora-3a,4a-diaza-s-indacene, the combination PHA-A-SPACER is preferably pentafluorobenzoyl, pentachlorobenzoyl, tetrafluorophthalimidyl or tetrachlorophthalimidyl. In embodiments where REPORTER is a coumarin, a resorufin or 4-bora-3a,4a-diaza-s-indacene the element SPACER in the combination A-SPACER is preferably not a single chemical bond. In all embodiments wherein REPORTER is a fluorescent 4-bora-3a,4a-diaza-s-indacene, REPORTER is not a blocked dye.

Applications of Polyhaloaryl-Substituted Reporters

The PHA-containing compounds of the invention are utilized by combining a sample of interest with the compound (according to methods generally known in the art) for a period of time sufficient for the probe to yield a detectable response under the desired conditions. Where the PHA-containing compounds are utilized for the detection of GSH or the activity of GST enzymes, in vitro or in vivo, the detectable response is the formation of a glutathione adduct. Where the PHA-containing compounds are utilized for analyzing the activity of enzymes other than glutathione transferases, the detectable response is typically an optical response. In another aspect of the invention, compounds of the invention that possess a polyfluorinated aryl that are GST substrates are incubated with an excess of both glutathione and GST in order to prepare isolated quantities of glutathione adducts of PHA dyes that are difficult to obtain otherwise.

Where the compounds of the invention are utilized for an assay for glutathione, the compound is combined with a sample of interest in the presence of an excess of a glutathione transferase. The sample is optionally a biological structure (e.g. a cell or cells), or a solution (including solutions that contain biological structures). In order for GST enzyme to act upon the substrates of the invention, it is necessary that the enzyme and glutathione be present with the substrate in the sample, typically in a solution of some type, even if the sample is not enclosed in a biological structure. The biological structure that encloses the sample is optionally a cell or tissue, and where the sample contains cells, the cells are optionally living, dead or dead and fixed using fixatives known in the art.

The suitability of a specific PHA-substituted compound a substrate for a GST enzyme is readily evaluated by comparing the conjugation of GSH to the substrate with and without the addition of the GST enzyme (Example 48). In an assay for the presence of GSH, the concentration of the polyfluorinated aryl-containing compound of the invention used for the assay is selected so as to be significantly above that of the highest concentration of glutathione in the sample. After a suitable period of time, as determined through control experiments in which a known amount of glutathione is assayed, the products are typically separated from the excess of the starting material by chromatography (e.g. thin layer chromatography (TLC), high performance liquid chromatography (HPLC), column chromatography, including affinity chromatography, paper chromatography or a similar means), electrophoresis (e.g. capillary zone electrophoresis, gel electrophoresis, paper electrophoresis, or a similar means) or by chemical extraction (in which the high polarity of the glutathione adduct favors higher solubility of the adduct in water relative to the PHA compound). Analysis of the products is by one of the optical, resonance or radioactive methods previously described.

In the assay of GST enzyme activity, glutathione and the fluorine-containing PHA compound are combined in large excess with the sample of interest. Following incubation for an appropriate time under appropriate reaction conditions, which time and conditions are pre-established using known samples of GST enzymes, the glutathione adduct is separated from any unreacted PHA compound and analyzed as described above. The GST assay samples can be obtained from cell extracts, from purified glutathione transferase isozymes (or mixtures of isozymes) or from glutathione transferase fusion proteins. In the latter case, the measurement of glutathione transferase activity can be used to assess the amount of fusion protein present in the sample. In addition, certain fluorine-containing PHA substrates can be used to qualitatively detect GST activity in live cells by incubation of the cells with the PHA substrate for an appropriate period of time then lysing the cells and analyzing the products as described above.

In another embodiment of the invention, the polyfluorinated compounds that are selective for glutathione are used to determine the efficiency of a cellular efflux pump of cells in a sample. The dye compound is used in the minimum concentration that gives a detectable signal. Typically, REPORTER is a fluorophore, chromophore, or a chemiluminescent precursor, or has the formula DYE-(BLOCK)$_a$, as described above. The efficiency of the cellular efflux pump of cells in the sample is determined by comparing the detectable signal of cells in the sample with the detectable signal in cells having a known efflux efficiency. Where the efflux pump is impaired, inhibited, or absent, the unblocked polyfluorinated compound is well retained in the cell; where the efflux pump is present and functioning, the signal from the polyfluorinated compound in the cells decreases markedly. Fluorescent and fluorogenic compounds are advantageous for monitoring the time course of the efflux pump.

The PHA moiety in the compounds of the invention generally permits simple incubation with the cells or tissues in normal culture medium. The required amount of probe (typically nanomolar to micromolar concentrations of probe in an aqueous or biocompatible solution) is determined by systematic variation in the amount or concentration of probe until a satisfactory response is detected. The detectable response is used to determine the presence, quantity, or the spatial or temporal distribution of components or a mechanism in a sample, according to known methods. The compounds of the invention are well-suited to the preparation of a kit comprising a PHA-substituted compound, optionally including materials for generating a standard response curve, and instructions for practicing any of the methods described herein.

The sample may comprise heterogeneous mixtures of biological components (e.g. intact cells, cell extracts, organelles, tissue homogenates, and mixtures thereof), or a single component or homogeneous group of components (e.g. natural or synthetic peptides or proteins). The cells, typically eukaryotic cells, preferably mammalian cells, may be present in an intact cell or in a medium that has been separated from the cell, such as biological fluids or cultures of essentially pure cells lines. The sample is optionally combined with other solutions in the course of staining, including wash solutions, permeabilization and/or fixation solutions, and other solutions containing additional detection reagents, according to known methods. Where the additional detection reagent has spectral properties that differ from those of the subject dye compounds, multi-color applications are possible.

After or during incubation and before, during or after separating the substrate from any enzymatic products, a sample containing a fluorescent or phosphorescent PHA-substituted compound is illuminated at a wavelength selected to give a detectable optical response, and observed with a means for qualitatively or quantitatively detecting the optical response, either visually or using a fluorometer, microscope, microplate reader, flow cytometer, laser scanner, hand lamp or other equipment. Typically the detectable optical response is a change in absorbance or fluorescence, preferably fluorescence, such as a change in the intensity or excitation or emission wavelength distribution of fluorescence, fluorescence lifetime, fluorescence polarization, or a combination thereof. PHA-substituted compounds that are chromophoric or chromogenic and are detected in an absorption spectrometer, a plate reader, using in-line detectors such as on a detector for chromatographic analyzers, visually or by other means. Radioactive glutathione adducts that have been separated from radioactive precursor substrates are analyzed by exposure to film or in a scintillation counter. Chemiluminescent precursors are treated with an enzyme or a chemical reagent as well known in the art to generate chemiluminescence and the resulting chemiluminescence is detected in a luminometer or by exposure of a film. Products to be analyzed by electron spin resonance or magnetic resonance are analyzed using an appropriate spectrometer.

In one aspect of the invention, the probes are combined with intact live cells and the fluorescence, phosphorescence or chemiluminescent signal that results from either direct staining or action of an enzyme is detected intracellularly or extracellularly, or in the cell extract following cell lysis, permeabilization and/or fixation by using the equipment described above. Probes in which $R^4$ is required to be F and at least 2 of $R^3$, $R^5$, and $R^6$ are also required to be F have been found to have the advantageous property of being well retained in cells at least partially through reaction with intracellular glutathione and to be at least partially retained in cells following fixation with formaldehyde or glutaraldehyde.

The PHA-substituted compounds of the invention in which the halogens are chloro or bromo, while being useful for permeabilization of the PHA substrate through cell membranes and for improving retention of products in cells (apparently through hydrophobic interactions rather than by formation of glutathione adducts, Example 65) do not react with glutathione either in vitro (Example 50) or in vivo (Example 67), even in the presence of excess GST enzymes. These retained compounds are optionally tracers or general viability indicators, or are substrates for specific enzymes. Particularly preferred are derivatives that comprise two identical BLOCK moieties that are acetate or a glycoside, such as β-D-galactopyranoside. As with their analogs that do not possess a PHA moiety, for example fluorescein diacetate (FDA) and fluorescein digalactoside (FDG), these derivatives can be used for detecting enzymes in live cells. However, the polyhaloaryl derivatives yield fluorescent products that are much better retained in cells than are the corresponding dyes, making them useful for cell tracing, as probes for study of cell efflux mechanisms and for detecting enzymatic activity in cells (Examples 58, 59, 61 and 62). Compounds that are particularly preferred for retention in cells possess a PHA moiety wherein each of $R^2$, $R^3$, $R^4$, $R^5$ and $R^6$ is F or Cl.

The compounds of the invention that are substrates for specific enzymes other than GST enzymes possess utility for detection of enzyme activity in a variety of samples. The analyte enzyme is optionally free in solution, immobilized in or on a solid or semi-solid material (such as a membrane (Examples 63 and 64) or an electrophoretic gel), extracted from a biological structure (e.g. from lysed cells, tissues, organisms or organelles), or remains enclosed within a biological structure, such as a cell or tissue. Where the analyte enzyme is present in a cell or cells, the cells may be living or fixed.

The enzyme substrates of the invention that are well-retained in cells are additionally useful in their ability to indicate that the cell is metabolically active. Furthermore, generation of different levels of fluorescence using the substrates of the invention in otherwise similar cells can indicate that the cells differ in their metabolism or their expression of the target enzyme and, thus, can be used to assess the overall health of the cell. Even though conjugation of the substrate to intracellular glutathione may improve retention of the DYE-(BLOCK)$_a$ moiety in the cell, it does not result in formation of a detectable reporter molecule unless the enzyme needed to remove the BLOCK is present and active. When the analyte enzyme is present, the fluorescent product is typically visible within a few minutes. Optimal accumulation, however, may require longer incubation. Compounds that form glutathione adducts may be pumped out of the cell through efflux mechanisms, but the compounds are typically retained in cells up to several hours or days, and through cell division. Cells containing the retained fluorescent metabolic products can be analyzed or sorted using a flow cytometer based on the detectable response of the DYE moiety. Where the detectable response of the DYE moiety indicates the presence or activity of an analyte enzyme, it may be used as the basis for isolating or discriminating cells using known techniques (e.g. as described by Melamed, et al., FLOW CYTOMETRY AND SORTING (2nd ed. 1990), incorporated by reference).

The presence or activity of the analyte enzyme, including GST and other enzymes, may be indicative of genetic content, a metabolic event, or the presence of an inhibitor of GST enzymes or of glutathione synthesis. For example, the measurement of enzyme activity in cells or cell extracts may be used to indicate the successful incorporation of genetic material responsible for enzyme expression or function into a cell or cells otherwise lacking the enzyme activity (e.g. as a result of transfection or transformation). Complete or partial loss of detectable substrate compounds from cells may be used to indicate loss of cell membrane integrity, e.g. in response to a lysing agent or cytotoxic event. Alternatively, loss of glutathione adducts from cells may be used to indicate drug or pesticide resistance.

The examples below are given so as to illustrate the practice of this invention. They are not intended to limit or define the entire scope of this invention.

EXAMPLES

Example 1

Preparation of 5-(pentafluorobenzoylamino) fluorescein (1) and 5-(benzoylamino)fluorescein (2):

5-Aminofluorescein (2 g, 5.8 mmol) is dissolved in 20 mL of anhydrous N,N-dimethylformamide (DMF) that contains anhydrous pyridine (0.94 mL, 11.6 mmol). To the solution is dropwise added 20 mL of an anhydrous dichloromethane solution of pentafluorobenzoyl chloride (1.3 mL, 8.7 mmol) at 0° C. under dry nitrogen protection. The resulting mixture is gradually warmed to room temperature and stirred overnight. This reaction mixture is concentrated in vacuo, and the residue is poured into water (200 mL). The precipitate thus formed is collected by filtration and washed with water.

The crude solid is redissolved in methanol (20 mL). To the solution is dropwise added 1M aqueous NaOH solution (6 mL, 6 mmol), and the resulting mixture is stirred at room temperature for 2 h. This reaction solution is neutralized with 10% HCl and concentrated in vacuo. The resulting suspension is diluted with water and filtered to collect the solid, which is then washed with water and air-dried. This treatment converts the diacylated and triacylated aminofluoresceins into the desired N-monoacylated product. The crude solid is recrystallized from ethyl acetate to afford Compound 1 as brown crystals (2.1 g, yield: 67%).

5-(Benzoylamino)fluorescein (Compound 2) is prepared similarly from 5-aminofluorescein and benzoyl chloride.

Example 2

Preparation of 5-(pentafluorobenzenesulfonylamino) fluorescein (3):

5-Aminofluorescein (1 g, 2.9 mmol) is dissolved in 10 mL of anhydrous DMF containing anhydrous pyridine (0.57 mL, 5.8 mmol). To the solution is added dropwise 10 mL of an anhydrous dichloromethane solution of pentafluorobenzenesulfonyl chloride (0.64 mL, 4.4 mmol) at 0° C. under dry nitrogen protection. The resulting mixture is gradually warmed up to room temperature and stirred overnight. This reaction mixture is concentrated in vacuo, and the residue is poured into water (100 mL). The precipitate that is formed is collected and washed with water.

The crude solid is redissolved in methanol (10 mL). To the solution is added dropwise 1M aqueous NaOH solution (3 mL, 3 mmol), and the resulting mixture is stirred at room temperature for 2 h. This reaction solution is neutralized with 10% HCl and concentrated in vacuo. The resulting suspension is diluted with water and filtered to collect the solid, which is then washed by water and air-dried. This treatment converts the diacylated and triacylated aminofluoresceins into the desired N-monoacylated product. The crude solid is chromatographed on a silica gel column using a gradient elution of chloroform/methanol to afford Compound 3 as a brown solid (652 mg, yield: 39%).

Example 3

Preparation of 5-(pentafluorobenzoylamino) fluorescein diacetate (4) and 5-(benzoylamino) fluorescein diacetate (5):

5-(Pentafluorobenzoylamino)fluorescein (1 g, 1.85 mmol) is dissolved in acetic anhydride (5 mL). To the solution is added dropwise anhydrous pyridine (0.37 mL). The resulting mixture is stirred at room temperature for 4 h and poured into ice-water (300 g). The precipitate that is formed is collected and washed with 1% HCl and water. The solid thus (Compound 4) obtained is air-dried (1.1 g, yield: 96%). 5-(Benzoylamino)fluorescein diacetate (Compound 5) is prepared similarly as a colorless solid starting with 5-(benzoylamino)fluorescein.

Example 4

Preparation of 5-pentafluorobenzoylaminofluorescein di-β-D-glucopyranoside, octaacetate (6):

5-(Pentafluorobenzoylamino)fluorescein (Compound 1, 1.5 g, 2.8 mmol) and acetobromo-α-D-glucose (3.42 g, 8.3 mmol) are dissolved in 1:1 anhydrous tetrahydrofuran/dichloromethane (120 mL). To the solution, $Ag_2CO_3$ (1.91 g, 6.9 mmol) and 3 Å molecular sieves (2 g) are added at once, and sym-collidine (0.84 g, 6.9 mmol) is added dropwise with stirring. The resulting mixture is stirred in the dark at room temperature for 4 days under dry argon protection and then diluted with chloroform (100 mL). The mixture is filtered through a pad of diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M $Na_2S_2O_3$ solution (2×250 mL), saturated $NaHCO_3$ solution (2×250 mL) and water (2×250 mL). The organic layer is dried over anhydrous $MgSO_4$ and evaporated in vacuo to give a yellow solid (primarily (5-pentafluorobenzoylamino)fluorescein mono-β-D-glucopyranoside, tetraacetate).

The crude 5-(pentafluorobenzoylamino)fluorescein mono-β-D-glucopyranoside, tetraacetate obtained above (presumably ~2.8 mmol) and $CdCO_3$ (1.2 g, 7.0 mmol) are suspended in freshly distilled toluene (150 mL). 50 mL of toluene is distilled off via a Dean-Stark trap. To the suspension is added dropwise 50 mL of anhydrous toluene solution of acetobromo-α-D-glucose (3.4 g, 8.3 mmol) under dry argon protection at 120°–140° C. The resulting mixture is gently heated at reflux for 6 h using the Dean-Stark trap to ensure anhydrous reaction conditions. The reaction mixture is cooled and concentrated under high vacuum. The residue is worked Lip with water (200 mL) and extracted with ethyl acetate (2×250 mL). The combined ethyl acetate layers are dried over anhydrous $Na_2SO_4$ and evaporated to afford a pale yellow porous solid. The crude solid is chromatographed on a silica gel column using a gradient elution of chloroform/acetonitrile to give Compound 6 as a colorless porous solid (2.1 g, yield: 64%).

Example 5

Preparation of 5-(pentafluorobenzoylamino) fluorescein di-β-D-glucopyranoside (7):

Compound 6 (1.25 g, 1.1 mmol) is dissolved in anhydrous methanol (50 mL) and cooled to 0° C. To the solution is slowly added 0.1M freshly prepared NaOMe in anhydrous MeOH (3×0.2 mL, 0.06 mmol) in 3 portions over 2 h under dry argon protection. The solution is stirred at 0° C. for 2 h, warmed to room temperature and stirred for 4 h. The reaction mixture is diluted with methanol (50 mL) and neutralized with AMBERLITE IRC-50 ion exchange resin ($H^+$ form) to pH 7.1. The mixture is filtered, and the resin is washed with methanol (2×25 mL). The combined filtrates are evaporated in vacuo to give an off-white solid. The crude material is redissolved in methanol (10 mL). To the solution is carefully added ether (200 mL) with shaking. The precipitate thus formed is collected by filtration under dry argon protection. This solubilization/precipitation process is repeated twice to afford Compound 7 as a colorless solid (838 mg, yield: 88%).

Example 6

Preparation of 5-(Pentafluorobenzoylamino) fluorescein di-β-D-galactopyranoside, octaacetate (8):

Compound 1 (1.0 g, 1.9 mmol) and acetobromo-α-D-galactose (2.3 g, 5.6 mmol) are dissolved in 1:1 anhydrous tetrahydrofuran/dichloromethane (100 mL). $Ag_2CO_3$ (1.3 g, 4.6 mmol) and 3 Å molecular sieves (2 g) are added at once to the solution, and then sym-collidine (0.56 g, 4.6 mmol) is added dropwise with stirring. The resulting mixture is stirred in the dark at room temperature for 4 days under dry argon protection and diluted with chloroform (100 mL). The mixture is filtered through a pad of diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M $Na_2S_2O_3$ solution (2×250 mL), saturated $NaHCO_3$ solution (2×250 mL) and water (2×250 mL). The organic layer is dried over anhydrous $MgSO_4$ and evaporated in vacuo to give a yellow solid (primarily 5-(pentafluorobenzoylamino)fluorescein mono-β-D-galactopyranoside, tetraacetate).

The crude 5-(pentafluorobenzoylamino)fluorescein mono-β-D-galactopyranoside, tetraacetate obtained above (presumably 1.9 mmol) and $CdCO_3$ (0.8 g, 4.7 mmol) are suspended in freshly distilled toluene (130 mL). 30 mL of toluene is distilled off via a Dean-Stark trap. To the suspension is added dropwise 50 mL of anhydrous toluene solution of acetobromo-α-D-galactose (2.3 g, 5.6 mmol) under dry argon protection at 120°–140° C. The resulting mixture is gently heated at reflux for 6 h while keeping, using the Dean-Stark trap to ensure anhydrous reaction conditions. The reaction mixture is cooled and concentrated under high vacuum. The residue is then worked up with water (200 mL) and extracted with ethyl acetate (3×100 mL). The combined ethyl acetate layers are dried over anhydrous $Na_2SO_4$ and evaporated to afford a pale yellow porous solid. The crude solid is chromatographed on a silica gel column using a gradient elution of chloroform/acetonitrile to give Compound 8 as a colorless porous solid (1.3 g, yield: 61%).

Example 7

Preparation of 5-(pentafluorobenzoylamino) fluorescein di-β-D-galactopyranoside (9):

Compound 8 (1.25 g, 1.1 mmol) is dissolved in anhydrous methanol (50 mL) and cooled to 0° C. To the solution is slowly added 0.1M freshly prepared NaOMe in anhydrous MeOH (3×0.2 mL, 0.06 mmol) in 3 portions over 2 h under dry argon protection. The solution is stirred at 0° C. for 2 h, warmed to room temperature and stirred for another 4 h. The reaction mixture is diluted with methanol (50 mL) and neutralized with AMBERLITE IRC-50 ion exchange resin ($H^+$ form) to pH 7.1. The mixture is filtered, and the resin is washed with methanol (2×25 mL). The combined filtrates are evaporated in vacuo to give an off-white solid. The crude material is redissolved in methanol (10 mL). To the solution is carefully added ether (200 mL) with shaking. The precipitate thus formed is collected by filtration under dry argon protection. This solubilization/precipitation process is repeated twice to afford Compound 9 as a colorless solid (982 mg, yield: 88%).

Example 8

Preparation of 5-(pentafluorobenzoylamino) fluorescein di-β-D-glucuronide, hexaacetate, dimethyl ester (10):

Compound 1 (800 mg, 1.5 mmol) and $CdCO_3$ (654 mg, 3.8 mmol) are suspended in freshly distilled toluene (100 mL). 30 mL of toluene is distilled off via a Dean-Stark trap. To the suspension is added dropwise 30 mL of anhydrous toluene solution of acetobromo-α-D-glucuronic acid, methyl ester (1.2 g, 3 mmol) under dry argon protection at 120°–140° C. The resulting mixture is gently heated at reflux for 6 h using the Dean-Stark trap to ensure an anhydrous reaction condition. The reaction mixture is cooled and concentrated under high vacuum. The residue is worked up with water (200 mL) and extracted with ethyl acetate (3×100 mL). The combined ethyl acetate layer is dried over anhydrous $Na_2SO_4$ and evaporated to afford a pale yellow porous solid. The crude solid is chromatographed on a silica gel column using a gradient elution of chloroform/ethyl acetate to give Compound 10 as a colorless porous solid (723 mg, yield: 41%).

Example 9

Preparation of 5-(pentafluorobenzoylamino) fluorescein di-β-D-glucuronide (11):

Compound 10 (700 mg, 0.59 mmol) is dissolved in methanol (10 mL), and the resulting solution is cooled to 0° C. To the solution, is dropwise added 1M precooled aqueous NaOH (5.31 mL, 5.31 mmol). The reaction mixture is stirred at 0° C. for 3 h and warmed to room temperature. This mixture is diluted with deionized water (40 mL) and neutralized with AMBERLITE IRC-50 ($H^+$ form) to pH 7.1. The resulting solution is concentrated in vacuo, and the residue is lyophilized to give a pale yellow solid. This crude solid is further purified on a SEPHADEX LH-20 column using 1:1 methanol/water as eluant to afford Compound 11 as a colorless solid (380 mg, yield: 72%).

Example 10

Preparation of 5-(pentafluorobenzoylamino) dihydrofluorescein diacetate (12):

Compound 1 (800 mg, 1.5 mmol) and Zn powder (1.3 g, 20 mmol) are suspended in 9:1 acetic anhydride/acetic acid. The suspension is heated at reflux for 3 h and cooled to room temperature. The reaction solution is worked up with water (200 mL) and extracted with ethyl acetate (3×100 mL). The combined ethyl acetate layer is dried over anhydrous $Na_2SO_4$ and evaporated to afford Compound 12 as a colorless solid (844 mg, yield: 92%).

Example 11

Preparation of N-(pentafluorobenzoyl)rhodamine 110 (13):

Rhodamine 110 (1.5 g, 4 mmol) and diisopropylethylamine (1.3 g, 10 mmol) are dissolved in anhydrous DMF (25 mL), and the resulting solution is cooled to −20° C. To the solution is added dropwise 2 mL of anhydrous dichloromethane solution of pentafluorobenzoyl chloride (1.1 g, 4.9 mmol) with stirring. The resulting mixture is stirred in the dark at −20° C. for 3 h under dry argon protection then warmed to room temperature. This reaction mixture is concentrated under high vacuum and worked up with water. The suspension formed is extracted with ethyl acetate (3×100 mL), and the combined organic layer is washed successively with 1M HCl solution (2×250 mL), water (1×250 mL), 1% M $NaHCO_3$ solution (2×250 mL) and water (2×250 mL). The ethyl acetate solution is dried over anhydrous $Na_2SO_4$ and evaporated in vacuo to give an red/brown solid. The crude solid is chromatographed on a silica gel column using 10:3:1 chloroform/ethyl acetate/ acetonitrile as eluant to give, following evaporation, Compound 13 as a brown solid (1.3 g, yield: 58%).

Example 12

Preparation of Rhodamine 110, pentafluorobenzoyl amide, tert-BOC-L-leucine amide (Compound 13-Leu-t-BOC):

Compound 13 (1.0 g, 1.8 mmol) and tert-BOC-L-leucine (1.3 g, 5 mmol) are dissolved in 1:1 anhydrous DMF/ pyridine (10 mL). To the solution is added 1-ethyl-3-[3-(dimethylamino)propyl]carbodiimide (955 mg, 5 mmol) with stirring. The resulting mixture is stirred in the dark at room temperature for 3 days under dry argon protection. This reaction mixture is concentrated under high vacuum and worked up with water (200 mL). The suspension thus formed is extracted with ethyl acetate (3×100 mL), and the combined organic layer is washed successively with 1M HCl solution (2×250 mL) and water (2×250 mL). The ethyl acetate solution is dried over anhydrous $Na_2SO_4$ and evaporated in vacuo to give an brown solid. The crude solid is chromatographed on a silica gel column using 10:1:1 chloroform/ethyl acetate/acetonitrile as eluant to give Compound 13-Leu-t-BOC as a colorless solid (212 mg, yield: 15%).

Example 13

Preparation of Rhodamine 110, pentafluorobenzoyl amide, L-leucine amide, hydrochloride (Compound 13-Leu):

Rhodamine 110, pentaflurobenzoyl amide, t-BOC-L-leucine amide (Compound 13-Leu-t-BOC; 100 mg, 0.13 mmol) is dissolved in trifluoroacetic acid (5 mL) at 0° C., and the resulting solution is stirred at the temperature for 30 min. This reaction solution is evaporated in vacuo to dryness. The residue is redissolved in methanol (2 mL), and 1M HCl/dioxane (0.15 mL, 0.15 mmol) is slowly added. To the solution is carefully added ether (10 mL) with shaking. The precipitate thus formed is collected by centrifugation. This solubilization/precipitation process is repeated twice to afford Compound 13-Leu as a colorless solid (48 mg, yield: 51%).

Example 14

Preparation of 2-(4'-t-BOC-1'-piperazinecarbonyl) resorcinol (14):

2,6-Dihydroxybenzoic acid (5.0 g, 32.5 mmol) and succinimidyl trifluoroacetate (7.4 g, 35 mmol) are dissolved in 9:1 anhydrous DMF/pyridine (10 mL). This reaction solution is stirred at room temperature overnight under dry argon protection. To the solution is added t-BOC piperazine (6.5 g, 35 mmol) with stirring. The resulting mixture is stirred at room temperature overnight. This reaction mixture is concentrated under high vacuum and worked up with water (500 mL). The suspension thus formed is extracted with ethyl acetate (3×500 mL), and the combined organic layer is washed successively with 1M HCl solution (2×500 mL) and water (2×500 mL). The ethyl acetate solution is dried over anhydrous $Na_2SO_4$ and evaporated in vacuo to give an off-white solid. The crude solid is recrystallized from ethyl acetate to give Compound 14 as a colorless solid (9.6 g, yield: 85%).

Example 15

Preparation of 2-piperazinecarbonylresorcinol (15):

Compound 14 (9 g, 28 mmol) is dissolved in trifluoroacetic acid (100 mL) at 0° C., and the resulting solution is stirred at room temperature for 2 h. This reaction solution is evaporated in vacuo to dryness. The residue is worked up with water. The precipitate formed is collected by centrifugation, washed by water and air-dried to give Compound 15 (5.7 g, yield: 92%).

Example 16

Preparation of 2-(4'-pentafluorobenzoyl-1'-piperazinecarbonyl)resorcinol (16):

Compound 15 (5 g, 22.5 mmol) is dissolved in 100 mL of anhydrous N,N-dimethylformamide (DMF) that contains anhydrous pyridine (2 mL, 25 mmol). To the solution is added dropwise 100 mL of anhydrous dichloromethane solution of pentafluorobenzoyl chloride (3.4 mL, 23 mmol) at 0° C. under dry nitrogen protection. The resulting mixture is gradually warmed to room temperature and stirred overnight. This reaction mixture is concentrated in vacuo, and the residue is poured into water (1 L). The precipitate thus formed is collected by filtration and washed by water.

The crude solid is redissolved in methanol (200 mL). To the solution is dropwise added 1M aqueous NaOH solution (25 mL, 25 mmol), and the resulting mixture is stirred at room temperature for 2 h. This reaction solution is neutralized with 10% HCl and concentrated in vacuo. This treatment converts the diacylated and triacylated by-products into the desired N-monoacylated product. The resulting suspension is diluted with water and filtered. The resulting solid is washed by water and air-dried to give Compound 16 (7.6 g, yield: 81%).

Example 17

Preparation of 8-chloro-3,7-dihydroxy-4-(4-pentafluorobenzoyl-1-piperazinecarbonyl) phenoxazine (17):

Compound 16 (7.0 g, 16.8 mmol) and 6-chloro-4-nitrosoresorcinol (2.9 g, 17 mmol) are suspended in methanesulfonic acid (100 mL). This reaction solution is heated and stirred at 80°–90° C. for 1 h. The reaction mixture is poured into ice-water (1 L). The suspension thus formed is extracted with ethyl acetate (3×500 mL), and the combined organic layer is washed successively with water (3×500 mL). The ethyl acetate solution is dried over anhydrous $Na_2SO_4$ and evaporated in vacuo to give a brown/red solid. The crude solid is chromatographed on a silica gel column using a gradient elution of chloroform/methanol to afford Compound 17 as a red solid (1.6 g, yield: 16%).

Example 18

Preparation of 8-chloro-3,7-dihydroxy-4-(4-pentafluorobenzoyl-1-piperazinecarbonyl) phenoxazine acetate (18):

Compound 17 (100 mg, 0.17 mmol) is dissolved in acetic anhydride (2 mL). To the solution is added anhydrous pyridine (1 drop). The resulting mixture is stirred at room temperature for 4 h and poured into ice-water (50 g). The precipitate thus formed is collected and washed by 1% HCl and water. The solid obtained is air-dried to give Compound 18 (105 mg, yield: 97%).

Example 19

Preparation of 8-chloro-3,7-dihydroxy-4-(4-pentafluorobenzoyl)-1-(piperazinecarbonyl) phenoxazine-β-D-glucopyranoside, tetraacetate (19):

Compound 17 (200 mg, 0.34 mmol) and acetobromo-α-D-glucose (280 mg, 0.68 mmol) are dissolved in 1:1 anhydrous tetrahydrofuran/dichloromethane (20 mL). To the solution is added at once $Ag_2CO_3$ (200 mg, 0.7 mmol) and 3 Å molecular sieves (1 g), and sym-collidine (845 mg, 0.7 mmol) is added dropwise with stirring. The resulting mixture is stirred in the dark at room temperature for 2 days under dry argon protection then diluted with chloroform (100 mL). The mixture is filtered through a pad of diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M $Na_2S_2O_3$ solution (2×250 mL), saturated $NaHCO_3$ solution (2×250 mL) and water (2×250 mL). The organic layer is dried over anhydrous $MgSO_4$ and evaporated in vacuo to give a brown solid. The crude solid is chromatographed on a silica gel column using a gradient elution of chloroform/acetonitrile to give Compound 19 as a yellow solid (227 mg, yield: 72%).

Example 20

Preparation of 8-chloro-3,7-dihydroxy-4-(4-pentafluorobenzoyl-1-piperazinecarbonyl) phenoxazine β-D-glucopyranoside (20):

Compound 19 (200 mg, 0.22 mmol) is dissolved in anhydrous methanol (5 mL) and cooled to 0° C. To the solution is slowly added 0.1M freshly prepared NaOMe in anhydrous MeOH (0.1 mL, 0.01 mmol) in 3 portions over 2 h under dry argon protection. The solution is stirred at 0° C. for 2 h, warmed to room temperature and stirred for 3 h. The reaction mixture is diluted with methanol (20 mL) and neutralized with AMBERLITE IRC-50 ion exchange resin (H⁺ form) to pH 7.1. The mixture is filtered, and the resin is washed with methanol (2×5 mL). The combined filtrate is evaporated in vacuo to give an off-white solid. The crude material is redissolved in methanol (2 mL). To the solution is carefully added ether (100 mL) with shaking. The precipitate formed is collected by filtration under dry argon protection. This solubilization/precipitation process is repeated twice to afford Compound 20 as a colorless solid (135 mg, yield: 81%).

Example 21

Preparation of 8-chloro-3,7-dihydroxy-4-(4-pentafluorobenzoyl-1-piperazinecarbonyl) phenoxazine β-D-galactopyranoside tetraacetate (21):

Compound 17 (200 mg, 0.34 mmol) and acetobromo-α-D-galactose (280 mg, 0.68 mmol) are dissolved in 1:1 anhydrous tetrahydrofuran/dichloromethane (20 mL). To the solution are added all at once Ag$_2$CO$_3$ (200 mg, 0.7 mmol) and 3 Å molecular sieves (1 g); sym-Collidine (845 mg, 0.7 mmol) is added dropwise with stirring. The resulting mixture is stirred in the dark at room temperature for 2 days under dry argon protection then diluted with chloroform (100 mL). The mixture is filtered through a pad of diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M Na$_2$S$_2$O$_3$ solution (2×250 mL), saturated NaHCO$_3$ solution (2×250 mL) and water (2×250 mL). The organic layer is dried over anhydrous MgSO$_4$ and evaporated in vacuo to give an brown solid. The crude solid is chromatographed on a silica gel column using a gradient elution of chloroform/acetonitrile to give Compound 21 as a yellow solid (240 mg, yield: 76%).

Example 22

Preparation of 8-chloro-3,7-dihydroxy-4-(4-pentafluorobenzoyl-1-piperazinecarbonyl) phenoxazine β-D-galactopyranoside (22):

Compound 19 (200 mg, 0.22 mmol) is dissolved in anhydrous methanol (5 mL) and cooled to 0° C. To the solution is slowly added 0.1M freshly prepared NaOMe in anhydrous MeOH (0.1 mL, 0.01 mmol) in 3 portions over 2 h under dry argon protection. The solution is stirred at 0° C. for 2 h, warmed to room temperature and stirred for 3 h. The reaction mixture is diluted with methanol (20 mL) and neutralized with AMBERLITE IRC-50 ion exchange resin (H⁺ form) to pH 7.1. The mixture is filtered, and the resin is washed with methanol (2×5 mL). The combined filtrates are evaporated in vacuo to give an off-white solid. The crude material is redissolved in methanol (2 mL). To the solution is carefully added ether (100 mL) with shaking. The precipitate thus formed is collected by filtration under dry argon protection. This solubilization/precipitation process is repeated twice to afford Compound 22 as a colorless solid (148 mg, yield: 89%).

Example 23

Preparation of 8-chloro-3,7-dihydroxy-4-(4-pentafluorobenzoyl-1-piperazinecarbonyl) phenoxazine β-D-glucuronide, triacetate, methyl ester (23):

Compound 17 (200 mg, 0.34 mmol) and acetobromo-α-D-glucuronic acid, methyl ester (270 mg, 0.68 mmol) are dissolved in 1:1 anhydrous tetrahydrofuran/dichloromethane (20 mL). To the solution are added all at once Ag$_2$O (162 mg, 0.7 mmol) and anhydrous Ca$_2$SO$_4$ (1 g); sym-Collidine (845 mg, 0.7 mmol) is added dropwise with stirring. The resulting mixture is stirred in the dark at room temperature for 2 days under dry argon protection and diluted with chloroform (100 mL). The mixture is filtered through a pad of diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M Na$_2$S$_2$O$_3$ solution (2×250 mL), saturated NaHCO$_3$ solution (2×250 mL) and water (2×250 mL). The organic layer is dried over anhydrous MgSO$_4$ and evaporated in vacuo to give a brown solid. The crude solid is chromatographed on a silica gel column using a gradient elution of chloroform/acetonitrile to give Compound 23 as a yellow solid (170 mg, yield: 57%)

Example 24

Preparation of 8-chloro-3,7-dihydroxy-4-(4-pentafluorobenzoyl-1-piperazinecarbonyl) phenoxazine β-D-glucuronide (24):

Compound 23 (150 mg, 0.16 mmol) is dissolved in methanol (2 mL), and the resulting solution is cooled to 0° C. To the solution is dropwise added 1M precooled aqueous NaOH (0.7 mL, 0.7 mmol). The reaction mixture is stirred at 0° C. for 3 h and warmed to room temperature. This mixture is diluted with deionized water (40 mL) and neutralized with AMBERLITE IRC-50 (H⁺ form) to pH 7.1. The resulting solution is concentrated in vacuo, and the residue is lyophilized to give a pale yellow solid. This crude solid is further purified on a SEPHADEX LH-20 column using 1:1 methanol/water as eluant to afford Compound 24 as a colorless solid (67 mg, yield: 54%).

Example 25

Preparation of 5-(pentafluorobenzoylamino) tetramethylrhodamine (25):

5-Aminotetramethylrhodamine (100 mg, 0.25 mmol) is dissolved in 10 mL of anhydrous tetrahydrofuran that contains anhydrous pyridine (1 mL, 12 mmol). To the solution is dropwise added 20 mL of anhydrous dichloromethane solution of pentafluorobenzoyl chloride (0.5 mL, 0.3 mmol) at 0° C. under dry argon protection. The resulting mixture is gradually warmed to room temperature and stirred for 4 h. This reaction mixture is concentrated in vacuo and poured into water (200 mL). The precipitate thus formed is collected and washed with water. The crude solid is chromatographed on a silica gel column using 10:1 chloroform/methanol as an eluant to afford Compound 25 as a red solid (80 mg, yield: 58%).

Example 26

Preparation of 5-(3',4',5'-trifluorobenzoylamino) fluorescein (26):

5-Aminofluorescein (100 mg, 0.29 mmol) is reacted with 3,4,5-trifluorobenzoyl chloride (87 mg, 0.45 mmol) at 0° C. under dry nitrogen protection, and worked up according to the procedure of Example 1. Compound 26 is obtained as a brown solid (105 mg, yield: 72%).

Example 27

Preparation of 5-(2'-carboxy-3',4',5',6'-tetrafluorobenzoylamino)fluorescein (27):

5-Aminofluorescein (1 g, 2.9 mmol) is dissolved in 10 mL of anhydrous N,N-dimethylformamide (DMF) that contains anhydrous pyridine (0.47 mL, 5.8 mmol). To the solution is added tetrafluorophthalic anhydride (660 mg, 3.0 mmol) in 5 portions over 5 h. The resulting mixture is stirred overnight. This reaction mixture is concentrated in vacuo, and the residue is poured into water (200 mL). The precipitate thus formed is collected by filtration and washed by water. The crude solid is taken up in 1M aqueous $NaHCO_3$ solution (100 mL), and the resulting mixture is filtered. The filtrate is washed with ether (3×100 mL). The aqueous layer is carefully neutralized to pH 7.5 with 10% HCl and the resulting precipitate is collected by filtration and air-dried to give Compound 27 (939 mg, yield: 59%).

Example 28

Preparation of 5-tetrafluorophthalimidylfluorescein (28):

Compound 27 (800 mg, 1.5 mmol) is suspended in concentrated $H_2SO_4$ (5 ml) and stirred at room temperature overnight. The suspension is poured into ice-water (200 g), and the resulting precipitate is collected by filtration and air-dried to give Compound 28 (844 mg, yield: 97%).

Example 29

Preparation of 7-diethylamino-4-(((Pentafluorobenzoyl)amino)methyl)coumarin (29):

4-Aminomethyl-7-diethylaminocoumarin (50 mg, 0.2 mmol) is treated with pentafluorobenzoyl chloride (0.5 mL, 0.3 mmol) at 0° C. under dry argon protection, and worked up according to the procedure of Example 25. Compound 29 is obtained as an off-white solid (67 mg, yield: 76%).

Example 30

Preparation of 4,4-difluoro-5,7-dimethyl-3-((((pentafluorobenzoyl)amino)ethyl)amino)carbonyl)-4-bora-3a,4a-diaza-s-indacene (30):

N-(4,4-Difluoro-5,7-dimethyl-4-bora-3a,4a-diaza-s-indacene-3-propionyl)ethylenediamine, hydrochloride (Molecular Probes, Inc., 10 mg, 0.02 mmol) is reacted with pentafluorobenzoyl chloride (0.5 mL, 0.3 mmol) at 0° C. in the presence of anhydrous pyridine under dry argon protection, and worked up according to the procedure of Example 25. A brown solid is obtained. The crude solid is further purified on TLC using 5:1:1 chloroform/acetonitrile/ethyl acetate as developing agent to give Compound 30 (6 mg, yield: 64%).

Example 31

Preparation of ((2-(pentafluorobenzoyl)amino)ethyl) ammonium trifluoroacetate (31):

t-BOC ethylenediamine (10 g, 62.5 mmol) and N,N-diisopropylethylamine (18.2 g, 141 mmol) are dissolved in anhydrous dichloromethane (200 mL), and the resulting solution is cooled to 0° C. The solution is added dropwise to 100 mL of an anhydrous dichloromethane solution of pentafluorobenzoyl chloride (21.5 g, 94 mmol). The resulting mixture is gradually warmed to room temperature and stirred for another 2 h. This reaction mixture is concentrated in vacuo, and the residue is poured into water (200 mL). The precipitate that forms is collected by filtration and washed with water. The crude material is purified by recrystallization from chloroform/hexane.

The t-BOC-protected material is dissolved in trifluoroacetic acid (200 mL), and stirred at room temperature for 4 h. The reaction mixture is concentrated in vacuo, the residue is redissolved in methanol (50 mL), and precipitated by adding ether (500 mL). The precipitate that forms is collected by filtration, washed with ether and dried in vacuo to afford Compound 31 as a colorless solid (22.7 g, yield: 85%).

Example 32

Preparation of 7-hydroxy-3-((((2-(pentafluorobenzoyl)amino)ethyl)amino)carbonyl) coumarin (32):

Compound 31 (7.7 g, 21.2 mmol) and 7-hydroxycoumarin-3-carboxylic acid, succinimidyl ester (6.6 g, 21.8 mmol) are dissolved in N,N-dimethylformamide (150 mL). To the solution is dropwise added 50 mL of a N,N-dimethylformamide solution of N,N-diisopropylethylamine (9 g, 70 mmol). The resulting mixture is gradually warmed to room temperature and stirred overnight. This reaction mixture is poured into water (1 L). The precipitate that forms is collected by filtration and washed with water. The crude material is recrystallized from ethyl acetate to afford Compound 32 as colorless crystals (8.9 g, yield: 95%).

Example 33

Preparation of 7-acetoxy-3-((((2-(pentafluorobenzoyl)amino)ethyl)amino)carbonyl) coumarin (33):

Compound 32 (650 mg, 1.5 mmol) and N,N-diisopropylethylamine (450 mg, 3.5 mmol) are dissolved in anhydrous N,N-dimethylformamide (10 mL). To the solution is dropwise added acetic anhydride (765 mg, 7.5 mmol). The resulting mixture is stirred at room temperature for 24 h then poured into ice-water (300 g). The precipitate that forms is collected, and washed with 1% HCl and water. The solid is recrystallized from N,N-dimethylformamide/ethyl acetate, and air-dried to give Compound 33 (510 mg, yield: 84%).

Example 34

Preparation of 3-((((2-(pentafluorobenzoyl)amino) ethyl)amino)carbonyl)umbelliferyl β-D-glucopyranoside, tetraacetate (34):

Compound 32 (1.2 g, 2.7 mmol) and acetobromo-α-D-glucose (1.5 g, 3.5 mmol) are dissolved in ethyl acetate (20 mL). To the solution are added all at once $Ag_2O$ (820 mg, 3.5 mmol) and 3 Å molecular sieves (2 g). Freshly redistilled quinoline (10 mL) is added dropwise with stirring. The mixture is stirred in the dark at room temperature for 4 days under dry argon and then diluted with chloroform (100 mL). The mixture is filtered through a pad of Diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M $Na_2S_2O_3$ solution (2×250 mL), saturated $NaHCO_3$ solution (2×250 mL) and water (2×250 mL). The organic layer is dried over anhydrous $MgSO_4$ and evaporated in vacuo to give a light brown solid. The crude material is purified on a silica gel column using 20:1 chloroform/methanol as eluant to afford Compound 34 a colorless solid (1.5 g, yield: 72%).

Example 35

Preparation of ((((3-(2-pentafluorobenzoyl)amino) ethyl)amino)carbonyl)umbelliferyl β-D-glucopyranoside (35):

Compound 34 (768 mg, 1.0 mmol) is dissolved in anhydrous methanol (50 mL), and cooled to 0° C. To the solution is slowly added 0.1M freshly prepared NaOMe in anhydrous MeOH (3×0.2 mL, 0.06 mmol) in 3 portions over 2 h under dry argon protection. The solution is stirred at 0° C. for 2 h, warmed to room temperature and stirred for 4 h. The reaction mixture is diluted with methanol (50 mL) and neutralized with AMBERLITE IRC-50 ion exchange resin ($H^+$ form) to pH 7.1. The mixture is filtered, and the resin is washed with methanol (2×25 mL). The combined filtrates are evaporated in vacuo to give an off-white solid. The crude material is redissolved in methanol (10 mL). To the solution is carefully added ether (200 mL) with shaking. The precipitate that forms is collected by filtration under dry argon protection. This solubilization/precipitation process is repeated twice to afford Compound 35 as a colorless solid (530 mg, yield: 88%).

Example 36

Preparation of ((((3-(2-pentafluorobenzoyl)amino) ethyl)amino)carbonyl)umbelliferyl β-D-galactopyranoside, tetraacetate (36):

Compound 32 (1.2 g, 2.7 mmol) and acetobromo-α-D-galactose (1.5 g, 3.5 mmol) are dissolved in ethyl acetate (20 mL). To the solution are added all at once, $Ag_2O$ (820 mg, 3.5 mmol) and 3 Å molecular sieves (2 g). Freshly redistilled quinoline (10 mL) is added dropwise with stirring. The resulting mixture is stirred in the dark at room temperature for 4 days under dry argon protection and then diluted with chloroform (100 mL). The mixture is filtered through a pad of diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M $Na_2S_2O_3$ solution (2×250 mL), saturated $NaHCO_3$ solution (2×250 mL) and water (2×250 mL). The organic layer is dried over anhydrous $MgSO_4$ then evaporated in vacuo to give a light brown solid. The crude material is purified on a silica gel column using 20:1 chloroform/methanol as eluant to afford Compound 36 as a colorless solid (1.2 g, yield: 58%).

Example 37

Preparation of ((((3-(2-pentafluorobenzoyl)amino) ethyl)amino)carbonyl)umbelliferyl β-D-galactopyranoside (37):

Compound 36 (710 mg, 0.9 mmol) is dissolved in anhydrous methanol (50 mL) and cooled to 0° C. To the solution is slowly added in 3 portions over 2 h under dry argon, 0.1M freshly prepared NaOMe in anhydrous MeOH (3×0.2 mL, 0.06 mmol). The solution is stirred at 0° C. for 2 h, warmed to room temperature and stirred for 4 h. The reaction mixture is diluted with methanol (50 mL) and neutralized with AMBERLITE IRC-50 ion-exchange resin ($H^+$ form) to pH 7.1. The mixture is filtered, and the resin is washed with methanol (2×25 mL). The combined filtrates are evaporated in vacuo to give an off-white solid. The crude material is redissolved in methanol (10 mL). To the solution is carefully added ether (200 mL) with shaking. The precipitate that forms is collected by filtration under dry argon protection. This solubilization/precipitation process is repeated twice to afford Compound 37 as a colorless solid (506 mg, yield: 93%).

Example 38

Preparation of ((((3-(2-pentafluorobenzoylamino) ethyl)amino)carbonyl)umbelliferyl β-D-glucuronide, triacetate, methyl ester (38):

Compound 32 (1.0 g, 2.3 mmol) and acetobromo-α-D-glucuronic acid, methyl ester (1.2 g, 2.8 mmol) are dissolved in ethyl acetate (20 mL). To the solution are added all at once $Ag_2O$ (630 mg, 3.5 mmol) and 3 Å molecular sieves (2 g). Freshly redistilled quinoline (10 mL) is dropwise added with stirring. The resulting mixture is stirred in the dark at room temperature for 4 days under dry argon protection and then diluted with chloroform (100 mL). The mixture is filtered through a pad of diatomaceous earth, and the residue is washed with chloroform (3×50 mL). The combined filtrates are evaporated in vacuo, and the residue is redissolved in chloroform (300 mL). The chloroform solution is washed successively with 1M HCl solution (2×250 mL), water (1×250 mL), 0.1M $Na_2S_2O_3$ solution (2×250 mL), saturated $NaHCO_3$ solution (2×250 mL) and water (2×250 mL). The organic layer is dried over anhydrous $MgSO_4$ and evaporated in vacuo to give a light brown solid. The crude material is purified on a silica gel column using 20:1 chloroform/methanol as eluant to afford Compound 38 as a colorless solid (920 mg; yield: 51%).

Example 39

Preparation of ((((3-(2-pentafluorobenzoylamino) ethyl)amino)carbonyl)umbelliferyl β-D-glucuronide (39):

Compound 38 (900 mg, 1.1 mmol) is dissolved in methanol (10 mL), and the resulting solution is cooled to 0° C. To the solution is dropwise added 1M precooled aqueous NaOH (5.5 mL, 5.5 mmol). The reaction mixture is stirred at 0° C. for 4 h then warmed to room temperature. This mixture is diluted with deionized water (40 mL) and neutralized with AMBERLITE IRC-50 ($H^+$ form) to pH 7.1. The resulting solution is concentrated in vacuo, and the residue is lyophilized to give a pale yellow solid. This crude solid is further purified on a SEPHADEX LH-20 column using 1:1 methanol/water as eluant to afford Compound 39 as a colorless solid (304 mg, yield: 42%).

Example 40

Preparation of 7-dimethylamino-4-(((((2-(pentafluorobenzoyl)amino)ethyl)amino)carbonyl) methyl)coumarin (40):

((2-(Pentafluorobenzoyl)amino)ethyl)ammonium trifluoroacetate (50 mg, 0.16 mmol) and 7-dimethylaminocoumarin-4-acetic acid, succinimidyl ester (98 mg, 0.15 mmol) are dissolved in anhydrous tetrahydrofuran (2 mL). To the solution is dropwise added N,N-diisopropylethylamine (111 mg, 1.1 mmol). The resulting mixture is gradually warmed to room temperature and stirred overnight. This reaction mixture is poured into water (50 mL), and extracted with ethyl acetate (2×50 mL). The combined organic layers are washed successively with 1M HCl solution (2×50 mL), water (1×50 mL), saturated $NaHCO_3$ solution (1×50 mL) and water (2×50 mL). The organic layer is dried over anhydrous $MgSO_4$ and evaporated in vacuo to give Compound 40 as a colorless solid. (66 mg, yield: 91%)

Example 41

Preparation of 7-hydroxy-3-pentafluorophenylcoumarin (41):

2,4-Dihydroxybenzaldehyde (3.7 g, 27.7 mmol) and ethyl pentafluorophenylacetate (10.6 g, 41.6 mmol) are dissolved in methanol (50 mL). To the solution is dropwise added piperidine (2.4 g, 28 mmol). The reaction mixture is heated at reflux for 4 h, and then cooled to room temperature. The precipitate that forms is collected by filtration and further purified by recrystallization from dioxane to give Compound 41.

Example 42

Preparation of 6,8-difluoro-7-hydroxy-3-pentafluorobenzoylcoumarin (42):

3,5-Difluoro-2,4-dihydroxybenzaldehyde (100 mg, 0.6 mmol) and ethyl pentafluorobenzoylacetate (268 mg, 0.9 mmol) are dissolved in methanol (5 mL). To the solution is dropwise added piperidine (106 mg, 1.3 mmol). The reaction mixture is heated at reflux for 6 h and then cooled to room temperature. The resulting mixture is concentrated in vacuo, and the residue is redissolved in chloroform (100 mL). The chloroform solution is washed successively with 1M HCl solution (2×250 mL), water (1×250 mL), saturated $NaHCO_3$ solution (2×250 mL) and water (2×250 mL). The organic layer is dried over anhydrous $MgSO_4$ and evaporated in vacuo to give a brown solid. The crude material is purified on a silica gel column using 20:1 chloroform/methanol as eluant to afford Compound 42 as a light yellow solid (180 mg, yield: 76%).

Example 43

Preparation of tetrafluorophthalhydrazide (43):

Tetrafluorophthalic anhydride (400 mg, 1.8 mmol) is dissolved in 10 mL of anhydrous N,N-dimethylformamide (DMF) that contains anhydrous pyridine (0.47 mL, 5.8 mmol). To the solution is slowly added hydrazine (64 mg, 2.0 mmol). The resulting mixture is stirred overnight. The reaction mixture is concentrated in vacuo, and the residue is poured into water (200 mL). The precipitate formed is collected by filtration, washed with water and air-dried to give Compound 43 (369 mg, yield: 87%).

Example 44

Preparation of 7-hydroxy-4-pentafluorophenylcoumarin (44):

Resorcinol (429 mg, 3.9 mmol) and ethyl pentafluorobenzoylacetate (1 g, 3.6 mmol) are suspended in methane sulfonic acid (10 mL), and heated at 70° C. for 2 h. The reaction mixture is poured into ice/water (200 g). The precipitate that forms is collected by filtration, and further purified by recrystallization from tetrahydrofuran to afford Compound 44 as a yellow solid (960 mg, yield: 83%).

Example 45

Preparation of 5-(4'-(S-glutathionyl))-(2',3', 5',6'-tetrafluorobenzoylamino)fluorescein (45):

Compound 1 (50 mg, 0.9 mmol) is suspended in 0.1M $K_2HPO_4$-$KH_2PO_4$ buffer (pH 8.0, 1 mL) that contains 1 mM EDTA. To the solution is added reduced glutathione (180 mg, 1.8 mmol) in 0.1M $K_2HPO_4$-$KH_2PO_4$ buffer (pH 8.0, 2 mL) and glutathione S-transferase (EC 2.5.1.18, Sigma Chemical) (5 mg in 1 mL of 0.1M $K_2HPO_4$-$KH_2PO_4$ buffer, pH 8.0). The resulting mixture is incubated at 37° C. with shaking for 6 h, and then mixed with 10% $H_2O_2$ to stop the reaction. The reaction mixture is lyophilized to afford a brown porous solid that is further purified on a SEPHADEX LH-20 column using deionized water as eluant to afford Compound 45 as an orange solid (26 mg, yield: 34%). The position of substitution of the S-glutathionyl moiety is determined by its characteristic $^{19}F$ magnetic resonance spectrum.

Example 46

Preparation of 5-(4'-(S-glutathionyl))-(2',3',5',6'-tetrafluorobenzoylamino)fluorescein di-β-D-glucopyranoside (46):

5-(Pentafluorobenzoylamino)fluorescein di-β-D-glucopyranoside (35 mg, 0.04 mmol) is dissolved in the mixture of 0.1M $K_2HPO_4$-$KH_2PO_4$ buffer (1.8 mL) that contains 1 mM EDTA and ethanol (0.2 mL). To the solution is added glutathione (60 mg, 0.06 mmol) in 0.1M $K_2HPO_4$-$KH_2PO_4$ buffer (2 mL) and glutathione S-transferase (EC 2.5.1.18) (5 mg) in 0.1M $K_2HPO_4$-$KH_2PO_4$ buffer. The resulting solution is incubated at room temperature with shaking for 6 h, and then mixed with 10% $H_2O_2$ to stop the reaction. The reaction mixture is lyophilized to afford a colorless porous solid that is further purified on a SEPHADEX LH-20 column using deionized water as eluant to afford Compound 46 as a colorless solid (29 mg, yield: 63%). The position of substitution of the S-glutathionyl moiety is determined by its characteristic $^{19}F$ magnetic resonance spectrum.

Example 47

Preparation of 5-(pentafluorobenzoylamino) fluorescein diphosphate, tetraammonium salt (47):

To a solution of Compound 1 (500 mg, 1 mmol) in anhydrous pyridine at 0° C. under dry nitrogen protection, is slowly added phosphorus oxychloride (300 mg, 3 mmol) with stirring. The resulting mixture is stirred in the dark at 0° C. for 4 h, and is then warmed to room temperature. The reaction solution is poured into ice-water (200 g), and extracted with ethyl acetate (2×250 mL). The aqueous layer was lyophilized, and the resulting solid was dissolved in water (10 mL) and neutralized with 1M ammonium hydroxide to pH 6.0. The aqueous solution is lyophilized again. The resulting crude solid is chromatographed on a SEPHADEX LH-20 column using a gradient elution of water/methanol to give Compound 47 as a colorless porous solid.

Example 48

Testing of Polyhalogenated Aryl (PHA) Derivatives as Glutathione Transferase Substrates:
Enzymatic Reaction:
To determine whether a compound is a selective substrate for glutathione transferase, a 2 mM ethanol stock solution of a polyhalogenated derivative (for example the series of butylbenzamides described in Example 49), reduced glutathione (phosphate buffer stock solution, 5 mM) and glutathione S-transferase (phosphate buffer stock solution, 1 unit/mL) are incubated at 25° C. in the mixture of 98% 0.1M $K_2HPO_4$-$KH_2PO_4$ buffer (pH7.5) that contains 1 mM EDTA and 2% ethanol for 2 h. The reaction is then stopped by adding 10% $H_2O_2$.

Blank Control:

The PHA compound (ethanol stock solution, 2 mM) and reduced glutathione (phosphate buffer stock solution, 5 mM) are incubated under the same conditions as described above without addition of glutathione S-transferase.

Separation by TLC and Detection:

Commercial precast silica gel TLC plates are used to follow both the enzymatic reaction and the blank control reaction. In general 3:1:1 butanol/methanol/water is used as a developing agent for relatively polar compounds, such as those that are xanthenes, glycosides and phosphates, and mixtures of chloroform and methanol are used to separate the relatively nonpolar compounds that do not have polar BLOCK groups, such as neutral coumarins, resorufins, 4-bora-3a,4a-diaza-s-indacenes, pyrenes, anthracenes, butylbenzamides and similar compounds. In every case the glutathione adduct is detected as a new, lower mobility spot of similar color and or fluorescence as the compound being tested. UV absorbance by the PHA substituent always permits detection of both the compound and any glutathione adduct by fluorescence quenching when the TLC sheet is illuminated with 254-nm radiation. Fluorescent compounds can be directly detected using appropriate UV or visible illumination. Provided that they have suitable absorption and/or fluorescence characteristics, test compounds and their glutathione adducts can also be detected (and often quantitated) on commercial scanners designed for scanning of TLC sheets, for instance as described in Example 53. Furthermore, the intensity of the signal on the TLC sheet often can be enhanced by methods well known in the art, such as by application of a phosphomolybdate spray, iodine vapors or a similar detection reagent. Radioactive products can be directly detected and quantitated by exposure to a suitable film using methods well known in the art.

Quantitation of TLC-separated Products:

Following separation of the substrate and the product by TLC, the products can be scraped from the sheet and then eluted with a suitable solvent (commonly methanol). Following separation from the silica gel and evaporation, the product is quantitated using the instrument most appropriate to the detection method, e.g. absorbance, fluorescence, NMR, ESR or (in the case of radiochemicals) scintillation counting. Chemiluminescence precursors can be activated by exposure to appropriate conditions to generate the luminescence, such as through addition of a strong base or an enzyme. In most cases the amount of product formed is compared to the amount of product spotted on the TLC sheet and/or to the amount of unreacted substrate to determine the overall suitability of a compound as a substrate. A time-course experiment can be conducted to measure the kinetics of the reaction.

Separation of Products by Chemical Extraction:

When the test compound is a relatively nonpolar derivative, such as a pyrene, anthracene or 4-bora-3a,4a-diazo-s-indacene, there is a considerable difference in the polarity of the substrate and the product. This can permit selective extraction of the more polar glutathione adduct into an aqueous or mostly aqueous layer, while retaining essentially all of the substrate in a layer of a mostly water-immiscible solvent, such as ethyl acetate, chloroform, methylene chloride or toluene. The suitability of this separation method for quantitative assays is easily tested by TLC or HPLC of the two layers (see below).

Separation and Detection of Products Using Other Separation Methods.

Methods other than TLC that separate the glutathione adduct from the test compound are also suitable for analysis of the suitability of a test compound as a selective substrate for glutathione transferase. In particular, high resolution methods such as HPLC (Example 52) and capillary electrophoresis are particularly suitable for both product detection and quantitation in the enzymatic reaction and the blank control. Furthermore, the ability to separate closely related compounds and to determine a characteristic retention time for each compound in either of these techniques can be used to demonstrate that the reaction in any assay for glutathione in a complex mixture that may contain thiols other than glutathione is selective for glutathnone.

Defining the Suitability of a PHA Derivative for Practice of the Method of the Invention.

Compounds that do not yield glutathione conjugates under the conditions in this example are judged to not be suitable substrates for either detection of glutathione or glutathione transferase activity, whereas compounds in the control reaction that react to a significant extent with glutathione in the absence of glutathione transferase are judged to be nonpreferred compounds for either assay, although they may still be suitable for practice of the method of the invention, provided that suitable control reactions and analyses are run.

Example 49

Synthesis of Halogenated N-butylbenzamides, and Evaluation as Glutathione Transferase Substrates:

A series of benzamide derivatives containing from 1 to 5 halogen substituents (as shown in Table 2) is synthesized as follows: the commercially available halogenated benzoyl chloride (1 mmol) in 5 mL chloroform is added dropwise to a solution of 1-aminobutane (5 mmol) in 10 mL chloroform in an ice bath. After 30 min the solution is washed with water, 1M HCl, 1M NaOH and water. After drying over anhydrous $Na_2SO_4$ the solution is evaporated and the colorless product is recrystallized from hexanes until TLC and NMR show it to be pure.

The benzamide derivatives are then evaluated as glutathione transferase substrates, using the procedure described in Example 48. Those compounds in Table 2 above the heavy line are not substrates for GST enzymes, while those below the heavy line formed a glutathione adduct when in the presence of both glutathione and a GST enzyme under suitable conditions.

TABLE 2

GSH/GST reactivities versus substitution patterns for polyhalogenated aryl moieties

| # of F atoms | | | | |
|---|---|---|---|---|
| 0 | pentachlorobenzene-CONHBu | | | |
| 1 | 4-F-C6H4-CONHBu | 3,5-Cl2-4-F-C6H2-CONHBu | | |
| 2 | 3,4-F2-C6H3-CONHBu | 3-Cl-4,5-F2-C6H2-CONHBu | 2,4-F2-C6H3-CONHBu | 3,4-F2-C6H3-CONHBu (F at 5) |
| 3 | 3,4,5-F3-C6H2-CONHBu | 2,4,5-F3-C6H2-CONHBu | 2,4,6-F3-C6H2-CONHBu | |
| 4 | 2,3,4,5-F4-C6H-CONHBu | 2,3,4,6-F4-C6H-CONHBu | 2,3,5,6-F4-C6H(CO2H)-CONHBu | tetrafluoro-N-butylphthalimide |
| 5 | F5-C6-CONHBu | | | |

Example 50

Reactivity of 5-pentafluorobenzoylamino) fluorescein (Compound 1) versus 5-(pentachlorobenzoylamino)fluorescein (Compound 48) with Glutathione Catalyzed by Glutathione Transferase:

The suitability of Compound 1 (Example 1) and 5-(pentachlorobenzoylamino)fluorescein (Compound 48) as substrates for glutathione transferase (GST) in the presence of excess glutathione (GSH) is tested in vitro as follows: 5 mM GSH, 0.5 mM substrate (Compound 1 or Compound 48) and 20 micrograms GST (Sigma #G-6511, 70 units/mg) are combined in 0.1M phosphate buffer, pH 8.0, for 1 hour at 37° C. The reaction is terminated by spotting approximately 3 μL on silica gel TLC plates. The plate is developed using 1-butanol: methanol: water (3:1:1). Examination of the TLC plate under long wavelength UV light reveals that Compound 1 forms a fluorescent adduct with glutathione with an $R_f$ of approximately 0.4. Compound 48 does not form a new adduct and the only spot detectable for Compound 48 corresponds to the unreacted compound, which migrates much closer to the solvent front. A control reaction in which GST is omitted yields very low or no reaction of either compound with GST. Analysis of the reaction mixture by HPLC as in Example 52 confirms that the reaction product of Compound 1 with GSH is identical to the authentic Compound 1-GSH adduct as prepared in Example 45 (Compound 45).

Example 51

Lack of Reactivity of Compound 1 with Thiol Groups of Proteins:

To test the specificity of the Compound 1 reaction with GSH versus thiol-containing proteins, β-galactosidase (a protein that has several free thiols) is dissolved at 5 mg/mL in deoxygenated 0.1M phosphate, 0.1M NaCl, pH 7.5, and reacted under anaerobic conditions with 5-(pentafluorobenzoylamino)fluorescein diacetate (Compound 4, Example 3) or Compound 1 dissolved at 10 mg/mL in DMSO at a molar ratio of the reagent to protein of 15. This assay is performed both in the presence and absence of 30 mM N-ethyl maleimide (NEM) as an effective thiol-blocking reagent. The reactions are incubated at room temperature for 1 hour, stopped by the addition of hydroxylamine, pH 9 to a final concentration of 0.15M, and incubated for 2 more hours to hydrolyze the acetate groups. Examination by TLC as in Example 48 shows no fluorescent spot at the origin, where the protein precipitates, in any of the samples, with or without the competing NEM. Consequently, no reaction of either Compound 4 or Compound 1 with β-galactosidase is detected under the described conditions. Examination by gel electrophoresis as in Example 67 confirms that no fluorescent proteins are formed with either reagent.

Example 52

Figure 1:
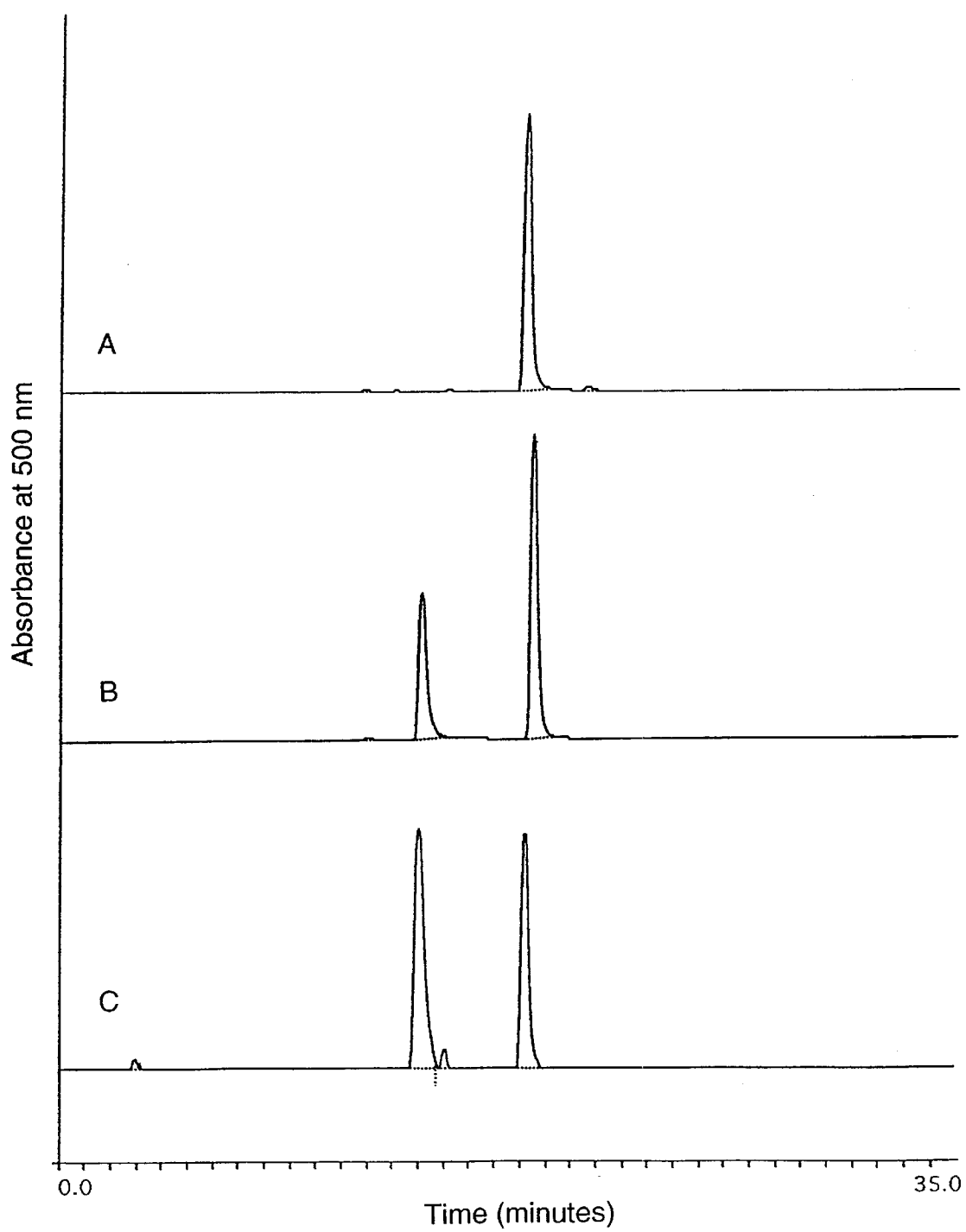
FIG. 1: High Performance Liquid Chromatography (HPLC) traces recorded as described in Example 52.

Analysis of the In Vitro Reaction Mixture by HPLC:

Reaction mixtures with and without GST using Compound 1 as the substrate, are prepared as described in Example 48. The solutions are mixed overnight with three volumes of ethyl acetate followed by centrifugation at 15,000×g for 30 min to separate the organic and aqueous layers. HPLC analysis using a Rainin HPLC equipped with a $C_{18}$, 5 μm, 100 Å, 4.6×250 mm MICROSORB-MV reverse phase column. Products are separated in 30 min with a gradient of 5% to 95% solvent B in Solvent A at a flow rate of 1 mL/min, where solvent A is 0.1M triethylammonium acetate, pH 7.0, and solvent B is acetonitrile (see FIG. 1). Products are detected by reading the absorbance at 500 nm. Peaks are identified and, if desired, quantitated by comparing retention times with authentic samples of the glutathione adduct of Compound 45 (Example 45). In this case, only one discrete peak with absorption at 500 nm corresponding to the unreacted substrate in the organic layer and two major peaks with elution times corresponding to the Compound 45 and to the unreacted Compound 1 in the aqueous layer are observed, typically due to incomplete extraction, although complete extraction of

Example 53

Analysis of the In Vitro Reaction Mixture Using a Plate Scanner:

Samples of the GST-catalyzed reaction products of Compound 1 with GSH are separated by TLC as described in Example 48. These are analyzed using a Molecular Dynamics STORM 860 automated plate scanner, which permits quantitation of spots by their fluorescence intensity (excitation at 450 nm). Data are analyzed using IMAGEQUANT software from Molecular Dynamics. The resulting plot of fluorescence intensity for the series of TLC spots is given in FIG. 2.

Example 54

Some Other Derivatives Tested as GSH/GST Substrates:

The suitability of a wide variety of PHA derivatives is tested by dissolving the test compound at 0.2–0.5 mM in 50 mM MOPS, pH 7.5, essentially as described in Example 48, and analyzing the product mixture using TLC. The following compounds are all found to give detectable glutathione adducts:

7-hydroxy-3-(pentafluorobenzoyl)coumarin
7-hydroxy-3-(pentafluorophenyl)coumarin
7-hydroxy-4-(pentafluorophenyl)coumarin
7-diethylamino-4-(((pentafluorobenzoyl)amino)methyl) coumarin
7-hydroxy-3-((((2-(pentafluorobenzoyl)amino)ethyl)amino) carbonyl)coumarin
7-dimethylamino-4-(((((2-(pentafluorobenzoyl)amino) ethyl)amino)carbonyl)methyl)coumarin
6,8-difluoro-7-hydroxy-3-pentafluorobenzoylcoumarin
5-(tetrafluorophthalimidyl)fluorescein
5-(3',4',5'-trifluorobenzoylamino)fluorescein
5-(2'-carboxy-3',4',5',6'-tetrafluorobenzoylamino) fluorescein
5-(pentafluorobenzoylamino)tetramethylrhodamine
8-chloro-3,7-dihydroxy-4-(4-pentafluorobenzoyl-1-piperazinecarbonyl)phenoxazine
8-chloro-3,7-dihydroxy-4-(4-pentafluorobenzoyl-1-piperazinecarbonyl)phenoxazine β-D-galactopyranoside
4,4-difluoro-5,7-dimethyl-3-[((((pentafluorobenzoyl) amino)ethyl)amino)carbonyl]-4-bora-3a,4a-diaza-s-indacene
((2-(pentafluorobenzoyl)amino)ethyl)ammonium trifluoroacetate tetrafluorophthalhydrazide.

Example 55

Use of Compound 1 to Quantitate GSH or GST Activity in Enzymatic Reactions:

A set of reactions as described in Example 48 are performed using limiting concentrations of GSH (0.1 μM–1 mM), to measure the range of sensitivity of the assay for quantitating GSH. Alternatively, the reaction is performed using excess GSH and limiting GST (0.1 μg/mL–20 μg/mL) to determine the suitability of the method to detect and quantitate glutathione transferase activity of isolated enzymes or of GST-fusion proteins.

In one hour reactions at 37° C., using 0.5 mM Compound 1 (Example 1) as the substrate, 10 μg/mL GST and limiting GSH, the minimum amount of fluorescent Compound 1-GSH adduct (Compound 45) detectable by simple illumination with a long wavelength UV hand lamp corresponds to ~2–4 picomoles of GSH. When using excess GSH and variable amounts of GST, it is possible to detect by visible inspection the reaction product in solutions containing 5 μg/mL of enzyme spotted on TLC in 2 μL amounts: this spot corresponds to ~10 ng of GST. In either assay the sensitivity can be increased by prolonging the incubation time. Quantitative measurement of the amount of product formed can be performed by either HPLC (Example 52), using a plate scanner (Example 53) or by extraction of the scraped silica gel spots into methanol or pH 8.0 buffer and measurement of the fluorescence against that of a series of dilutions of the authentic adduct (Example 45) in the same buffer using a fluorometer or microplate reader.

Example 56

Use of Compound 1 to Quantitate Glutathione (GSH) or Glutathione Transferase (GST) Activity in Cell Extracts:

Cultures of BPAE cells are trypsinized, pelleted, washed once in PBS and resuspended in 200 μL of distilled water in numbers from 200 to 1,000,000. The cells are lysed by repeated freezing and thawing and spun for 10 min. in a microfuge to eliminate the insoluble particles from the lysate, which contains both GSH and GST.
Determination of GSH.

To 150 μL of the lysate are added 5.5 μL of 1.8M MOPS pH 7.5, Compound 1 at the final concentration of 0.2 mM, 5 μg GST and distilled water to obtain the final volume of 200 μL. The reaction mixtures are incubated for 2 hours at 37° C. and analyzed by TLC by spotting 2 μL of each sample and developing as described in Example 48. The spots corresponding to the product formed by the different amounts of cells, because of their endogenous GSH is quantitated on a plate scanner as described in Example 53. The plot of the fluorescence intensity of the Compound 1-GSH adduct versus the number of cells shows good linearity, confirming the suitability of this compound for quantitation of not only GSH in general, but also average intracellular GSH (FIG. 3). Quantitation of GSH can also be performed by separating the product from the reaction mixture by HPLC as in Example 52.
Determination of GST activity.

The assay for the amount of GST activity present in cell lysates (endogenous GST) is performed using the same system as above with the exception that 5 mM GSH is added to the reaction mixture to ensure that there is a sufficient excess of GSH to saturate the enzyme. The reaction is incubated for one hour at 37° C. and 2 μL of each sample are spotted on TLC plates and developed as described in Example 48. Product formation is quantitated using a plate scanner as for GSH determination (as in Example 53). Since at high concentration of both substrate and GSH a trace amount of adduct forms, even in absence of enzyme, the area corresponding to the amount of product formed in absence of cells (background) is subtracted from the other areas and the results plotted as above. The results show that Compound 1 is useful for the determination of the activity of GST activity in cells lysates (FIG. 4). Similarly, this assay system can be used to quantitate GST-fusion proteins.

Example 57

Use of PFB Rhodamine 110 Derivatives as Peptidase Substrates In Vitro:

Activity of trypsin in vitro is most conveniently assayed in a CYTOFLUOR II fluorescence plate reader. Protease substrates are prepared following the methods given in Examples 12 and 13. The stock reagents required are: 1) Compound 13-CBZ-Arg substrate, 10 mM in DMSO, diluted 1:100 in reaction buffer to a 0.1 mM solution; 2) Compound 13-CBZ-Ile-Pro-Arg substrate, 10 mM in DMSO, diluted 1:100 in reaction buffer to 0.1 mM solution; 3) Compound 13-CBZ-Pro-Arg substrate, 10 mM in DMSO, diluted 1:100 in reaction buffer to 0.1 mM solution; 4) Reaction buffer: 0.05M TRIS, 0.01M $CaCl_2$ pH 8; 5) Trypsin, Type I from bovine pancreas (Sigma #T-8003) at dilutions of 50 units/mL, 5 units/mL, 0.5 units/mL and 0 units/mL in reaction buffer. To conduct the assay 75 μL of each of the substrates is added to four wells of a row in the microplate. To each of the substrate solutions is added 75 μL of a trypsin solution such that the final concentration of the substrate in each well is 50 mM and that of the enzyme is 25 units/mL or 2.5 units/mL or 0.25 units/mL or 0 units/mL. The last well of each series with no enzyme serves as a control to determine the amount of nonspecific cleavage and background fluorescence. The plate is allowed to incubate at 37° C. for 35 minutes. Fluorescence of each well is determined using a 485 nm excitation filter, a 530 nm emission filter and gain setting of 30.

Using the above conditions, for each of the three substrates tested there is at least a 20-fold increase in fluorescence at an enzyme concentration of 25 units/mL, at least a 10-fold increase in fluorescence at an enzyme concentration of 2.5 units/mL, and at least a 3-fold increase in fluorescence at an enzyme concentration of 0.25 units/mL as compared to the fluorescence of the solution without any enzyme.

Example 58

Use of PFB Rhodamine 110 Derivatives as Peptidase Substrates In Vivo as Detected by Flow Cytometry:

P3×63AG8 cells obtained from American Type Culture Collection Co., Rockville, Md. are used. They are grown in a humidified atmosphere of 5% $CO_2$ in Dulbecco's modified Eagle's medium (D-MEM) supplemented with 10% calf serum, 50 μg/mL gentamycin, 300 μg/mL L-glutamine and 10 mM HEPES, pH 7.4. Compound 13-Arg (Prepared as in Examples 12 and 13) is dissolved at 1 mM in DMSO. The P3×63AG8 cells are trypsinized, washed with phosphate-buffered saline (PBS), pH 7.2 and resuspended in 1 mL of the same buffer. 1 μL of the stock reagent is added to 1 mL of the cell suspension to obtain a final concentration of 1 μM. Incubation is carried out at 37° C. for 30 minutes. Cells are centrifuged to form a pellet, the supernatant is discarded, the cells are washed twice with PBS, pH 7.2 and resuspended in 300 μL of the same buffer. Cells are analyzed by flow cytometry using the Becton-Dickinson FACS Vantage flow cytometer. Cells stained with the Compound 13-Arg substrate are detected in the FL 1 (530±30 nm) channel and exhibit fluorescence levels greater than the cell's autofluorescence.

Example 59

Use of PFB Rhodamine 110 Derivatives as Peptidase Substrates In Vivo as Detected Using a Microscope:

CRE BAG 2 cells obtained from American Type Culture Collection Co., Rockville, Md. are used. They are grown in a humidified atmosphere of 5% $CO_2$ in D-MEM supplemented with 10% calf serum, 50 µg/mL gentamycin, 300 µg/mL L-glutamine and 10 mM HEPES, pH 7.4. 1 mM stock solutions of Compound 13-Leu (Example 13) and Compound 13-Arg substrate are prepared in DMSO. CRE BAG 2 cells are trypsinized, washed with phosphate-buffered saline, pH 7.2 and resuspended in 1 mL of the same buffer. 1 µL, 0.5 µL or 0.1 µL of the stock reagents is added to 1 mL of the cell suspension to obtain a final concentration of 1 µM, 0.5 µM or 0.1 µM. Incubation is carried out at 37° C. for 30 minutes. Cells are centrifuged to form a pellet, the supernatant is discarded and the cells are washed with PBS, pH 7.2 and suspended in the same buffer. Cells are mounted on slides and observed by fluorescence microscopy using filters optimized for fluorescein. Stained cells typically show punctate green fluorescence associated with organelles.

Example 60

Analysis of a Glycosidase Enzyme In Vitro:

The stock reagents required are: 1) Compound 9 (Example 7) 5 mM in ethanol; 2) Reaction buffer: 0.3M potassium phosphate, 3 mM $MgCl_2$ pH 7.5; 3) β-galactosidase (Boehringer-Mannheim), dissolved at 10 mg/mL in 0.05M potassium phosphate, pH 7; 4) Enzyme diluent: 0.01M Tris HCl, 0.01M $MgCl_2$, 0.01M NaCl, 0.01M β-mercaptoethanol, pH 7.5. 130 µL of the reaction buffer is added to a series of rows and columns in a microplate. To each of the wells with reaction buffer is added 10 µL of the substrate solution. The enzyme stock solution is diluted to 1 mg/mL, 0.1 mg/mL, 10 µg/mL, 1 µg/mL, 0.1 µg/mL and 0 µg/mL. To the wells containing reaction buffer and substrate, 10 µL of each of the different concentration enzyme solutions is added. The wells containing 0 µg/mL enzyme serve as controls. The plate is allowed to incubate at room temperature for 20 minutes. Fluorescence of each well is determined using a 485 nm excitation filter, a 530 nm emission filter and gain setting of 40. Using the above conditions, as little as 6.7 ng/mL enzyme can be detected using the substrate at 333 µM concentration. The fluorescence response is linear until the enzyme concentration reaches ~6.7 µg/mL.

Example 61

Use of Compound 9 to Detect β-galactosidase Activity and for lacZ Detection in Cells by Microscopy:

NIH-3T3 cells (lacZ negative) and CRE BAG 2 cells (lacZ positive) are obtained from American Type Culture Collection Co., Rockville, Md. They are grown in a humidified atmosphere of 5% $CO_2$ in D-MEM supplemented with 10% bovine calf serum, 50 µg/mL gentamycin, 300 µg/mL L-glutamine and 10 mM HEPES, pH 7.4. A 50 µM stock solution of Compound 9 is prepared in water: dimethylformamide (DMF) (1:1). NIH-3T3 and CRE BAG 2 cells are trypsinized, washed and suspended in D-MEM containing 10% BCS. 10 µL of the cell suspension is added to 0.989 mL of the same medium. 1 µL of the 50 µM substrate solution is added to the cells to obtain a final concentration of 50 nM. Incubation is carried out at 37° C. for 35 minutes. Cells are centrifuged to form a pellet, supernatant is discarded and cells are resuspended in D-MEM with 10% BCS. Cells are mounted on slides and observed by fluorescence microscopy. NIH-3T3 cells show green fluorescent lysosomes with very little cytoplasmic background. The CRE BAG 2 cells show green fluorescent lysosomes with well-stained green fluorescent cytoplasm.

Example 62

Use of a PHA-coumarin Galactoside to Measure the Level of Marker Gene Expression in Cells by Flow Cytometry and Comparison with a Chloromethylcoumarin Galactoside:

NIH-3T3 and CRE BAG2 cells are maintained as in Example 61. A 10 mM stock solution of (((3 -(2-pentafluorobenzoyl)amino)ethyl)amino)carbonyl)-umbelliferyl β-D-galactopyranoside (Compound 37; Example 37) is prepared in DMF. A 10 mM stock solution of 4-chloromethylcoumarin β-D-galactopyranoside (CMCG; Molecular Probes #D-2921) is prepared in a 1:1 mixture of DMSO and water. NIH-3T3 and CRE BAG2 cells are trypsinized, washed with phosphate buffered saline (PBS), pH 7.2 and resuspended in D-MEM with 10% BCS. To separate 1 mL cell suspensions are added the dye stock solutions to obtain final concentrations of 0.2 mM dye. Incubation is carried out at 37° C. for 30 minutes. Cells are centrifuged to form a pellet, the supernatant is discarded and the cells are washed twice with PBS, pH 7.2 and suspended in the same buffer. Cells are analyzed by flow cytometry using a Becton-Dickinson FACS Vantage flow cytometer. The NIH-3T3 cells stained with the Compound 37 do not show fluorescence greater than that observed for autofluorescent cells. The same is true for NIH-3T3 cells stained with CMCG. However, CRE BAG 2 cells stained with the Compound 37 show fluorescence that is greater than 25-fold that shown by autofluorescent control cells. For the CRE BAG 2 cells stained with CMCG, the fluorescence intensity is only 8-fold greater than that of the autofluorescent control cells.

Example 63

Detection of Alkaline Phosphatase on a Membrane Blot:

The reagents used are: 1) 5-(pentafluorobenzoylamino) fluorescein diphosphate, tetraammonium salt (Compound 47; Example 47), 10 mM in 0.1M Tris, pH 8.5; 2) fluorescein diphosphate (FDP; Molecular Probes, #F-2999), 10 mM in 0.1M Tris, pH 8.5; 3) BLOCKER Blotto in PBS (Pierce Chemical Company); 4) 0.2M glycine, pH 8.8; 5) 0.05M $MgCl_2$, 6) 0.1M Tris, pH 8.5; 7) wash buffer: 20 mM Tris, 137 mM NaCl, 0.5% TWEEN 20, pH 7.5. Stock solutions of alkaline phosphatase are diluted in 0.1M Tris, pH 8.5 to obtain solutions with the following concentrations: 1 µg/µL, 0.5 µg/µL, 0.25 µg/µL, 0.1 µg/µL, 50 ng/µL, 10 ng/µL, 1 ng/µL and 0 ng/µL. 1 µL of each diluted solution is spotted on a nitrocellulose membrane (1"×1"), pore size 0.45 µM, and allowed to dry overnight at room temperature. Blocking is done by treating both nitrocellulose blots with 2 mL of supernatant liquid from the BLOCKER Blotto solution for 30 minutes at room temperature. The following mixture is prepared: 1.5 mL of 0.2M glycine, pH 8.8+0.4 mL of 0.05M $MgCl_2$+100 µL of 0.1M Tris, pH 8.5+10 µL of 10 mM substrate stock solution (either PFB-FDP or FDP). Blotto supernatant on the blots is replaced with the above mixture and incubation is carried out for 35 minutes at 37° C. A Polaroid image of the blots is obtained by illuminating with reflected UV light at 254 nm. Exposure time is 5–10 sec with an aperture setting of F=4.5 and filter #15 is used to block unwanted light. Both Compound 47 and FDP can detect ~50 ng of the enzyme prior to washing the membranes. The blots are washed twice for 5 minutes each time with 2 mL of wash buffer and an image is obtained using the same settings and exposure times as described above. FDP is unable to detect the presence of any enzyme while Compound 47 is able to detect ~50 ng of the enzyme per spot.

Example 64

Detection of β-D-galactosidase on a Membrane Blot:

The reagents used are: 1) Compound 9, 5 mM in ethanol; 2) β-D-galactosidase, 10 mg/mL in 0.05M potassium phosphate, pH 7; 3) Enzyme diluent: 0.01M Tris, 0.01M $MgCl_2$, 0.01M mercaptoethanol, 0.01M NaCl, 1% BSA, pH 7.5; 4) 1% BSA in PBS, pH 7.2; 5) Reaction buffer: 0.3M potassium phosphate, 3 mM $MgCl_2$, pH 7.5; 6) Wash buffer: 20 mM Tris, 137 mM NaCl, 0.5% Tween 20, pH 7.5. A stock solution of β-galactosidase is diluted in enzyme diluent to obtain solutions with the following concentrations: 1 µg/µL, 0.1 µg/µL, 0.01 µg/µL, 1 ng/µL, 0.1 ng/µL and 0 ng/µL. 1 µL of each diluted solution is spotted on a two nitrocellulose membranes (1"×1"), pore size 0.45 µM, and dried immediately by blowing argon on the membranes. One of the membranes is blocked by treatment with 1% BSA in PBS for 20 minutes at room temperature. The following mixture is prepared: 4.95 mL of reaction buffer+50 mL of Compound 9 stock solution. 2 mL of this solution is added to each of the blots and incubation is carried out at room temperature for 1 hour. The blots are washed once with 2 mL of wash buffer. 0.5 mL of the mixture described above is once again added to the blots and incubation is carried out at room temperature for 30 minutes. The blots are allowed to dry and an image is obtained by illuminating with reflected UV light at 254 nm. The exposure time is 10 sec with an aperture setting of F=4.5 and filter #9 is used to block unwanted light. The use of Compound 9 is able to detect the presence of ~100 ng of enzyme under these conditions.

Example 65

Hydrolysis of Esterase Substrates and Product Retention in Live Cells:

NIH-3T3 cells obtained from American Type Culture Collection Co., Rockville, Md. are used. They are grown in a humidified atmosphere of 5% $CO_2$ in D-MEM supplemented with 10% bovine calf serum (BCS), 50 µg/mL gentamycin, 300 µg/mL L-glutamine and 10 mM HEPES, pH 7.4. Stock solutions of Compound 4 (Example 3), 10 mM in DMSO, and Compound 48 (Example 50), 5 mM in DMSO, are prepared. NIH-3T3 cells are trypsinized, washed with phosphate-buffered saline (PBS), pH 7.2 and resuspended in D-MEM with 10% BCS. To 1 mL of the cell suspension is added the dye stock solution to obtain a final dye concentration of 0.1 mM. Incubation is carried out at 37° C. for 30 minutes followed by incubation on ice for 30 minutes. Cells are centrifuged to form a pellet, the supernatant is discarded and the cells are washed twice with PBS, pH 7.2 and suspended in the same buffer. Cells are analyzed by flow cytometry using the Becton-Dickinson FACS Vantage flow cytometer. After analysis on the flow cytometer, cells are placed at 37° C. and analyzed by flow cytometry at frequent intervals over a period of 75 minutes. Cells stained with either of the dyes are at least 20-fold brighter than the autofluorescent control cells. Approximately 45% of Compound 4 and 35% of Compound 48 are still retained by the cells after 75 minutes of incubation at 37° C.

Example 66

Glutathione Adduct Formation in Cultured Animal Cells:

Bovine pulmonary aorta endothelial cells (BPAEC) are removed from flasks by trypsinization and washed into fresh complete growth medium to yield $10^6$ cells/mL. One mL aliquots of the cell suspension are incubated with 5 µM 5-benzoylaminofluorescein diacetate (Compound 5, Example 3) or 5-(pentafluorobenzoylamino)fluorescein diacetate (Compound 4, Example 3) for either 15 min or for 4 hr at 37° C. without washing. Other aliquots of the cell suspension are loaded with the same substrates for 1 hour, rinsed into fresh complete medium, then incubated in the absence of substrate for an additional 3 hr at 37° C. to look for retention and efflux of fluorescent products. At the end of each incubation period the cells are removed by centrifugation and the supernate is retained. The cell pellets are resuspended in 1 mL of E-Pure water and subjected to three freeze-thaw cycles (–80° C. to 37° C.). The original medium supernate and the lysed cell pellets are lyophilized and resuspended in equivalent volumes of water for analysis by HPLC as described in Example 52 and shown in FIG. 1. Data in Table 3 represent the fate of the substrate that has passed through the intracellular compartment, resulting in generation of fluorescent dye species (both the hydrolyzed dye (Compound 1) and its glutathione adducts, if any) through cleavage of the acetate moieties. It is observed that Compound 4 gives rise to glutathione (GSH) adducts and, as expected, the Compound 5 substrate does not. The GSH adduct of Compound 1 is rapidly removed from the cytoplasm of these BPAEC cells but a fraction of the fluorescence labeling is retained, even after 4 hours. This is true both for cells that have been held in the presence of the polyfluorinated substrate for 4 hours and those that have been washed free of this compound after 1 hour. The hydrolysis product of Compound 5 is not detectable in cells that have been washed at one hour then incubated for an additional 3 hours. This demonstrates the improved retention of the polyfluorinated product in live cells.

Cells labeled separately with Compound 5 and Compound 4 are fixed with 3.7% formaldehyde in phosphate-buffered saline (PBS) for 30 minutes, permeabilized with 0.2% Triton X-100 in PBS for 30 minutes, and rinsed in PBS. Cells originally stained with Compound 5 are essentially nonfluorescent, whereas cells stained with Compound 4 remain appreciably fluorescent.

TABLE 3

The fate of 5-(pentafluorobenzoylamino)fluoresceins and 5-(benzoylamino)fluoresceins in cultured bovine pulmonary endothelial cells.

|  | TIME | INTRACELLULAR | | EXTRACELLULAR | |
|---|---|---|---|---|---|
|  |  | GSH adduct | Free dye | GSH adduct | Free dye |
| Compound 4* | 15 min. | 72 (1.9%) | 237 (6.3%) | 97 (2.6%) | 3350 (89.2%) |
|  | 4 hrs | 21 (0.4%) | 23 (0.4%) | 642 (12.4%) | 4498 (86.8%) |
|  | 1 hr.‡ washed | <1 (<0.2%) | <1 (<0.2%) | 62 (14.7%) | 361 (85.3%) |
| Compound 5† | 15 min | ND | 450 (8.5%) | ND | 4829 (91.5%) |
|  | 4 hrs | ND | 78 (0.9%) | ND | 8627 (99.1%) |
|  | 1 hr.‡ washed | ND | ND | ND | 469 (100%) |

Numbers represent relative fluorescence units. Percentages (in parentheses) are the fraction of fluorescence in each compartment with respect to the total fluorescence detected in both the cell lysate and supernate.
*5-(pentafluorobenzoylamino)fluorescein diacetate
†5-benzoylaminofluorescein diacetate
‡Cells were incubated continuously with the substrates for 15 min or 4 hr. Alternatively, the cells were incubated with the substrates for 1 hr, rinsed into fresh medium, then incubated at 37° C. for an additional 3 hr (T = 1 hr, washed).

Example 67

Analysis of the Intracellular Products of Various Tracers:

Cultures of either 3T3 or BPAE cells are treated with 5 $\mu$M solutions of either Compound 4,5-(pentachlorobenzoylamino)fluorescein diacetate, 5-pentafluorobenzenesulfonylamino)fluorescein diacetate, or 5-chloromethylfluorescein diacetate (CMFDA, Molecular Probes, Inc.) for 1 hr at 37° C. The cells are spun, resuspended in distilled water and lysed by repeated freezing and thawing. 20 $\mu$L of the cell lysate supernatant is diluted with 30 $\mu$L of SDS-PAGE sample buffer, containing β-mercaptoethanol. The cell pellets are dispersed in 50 $\mu$L of water. 20 $\mu$L of each sample is added to 30 $\mu$L of the same sample buffer. The samples are heated at 95° C. for 5 min. and loaded on 4–20% polyacrylamide gradient minigels. At the completion of the run the gels are observed with UV excitation. Two closely spaced green fluorescent bands were observed in the region of the tracking dye for Compound 4 and 5-pentafluorobenzenesulfonylamino)fluorescein diacetate, possibly corresponding to the GSH-adducts and to Compounds 1 and 3, respectively. No other band corresponding to proteins is visible in the lane of either sample. The lane corresponding to the cells loaded with CMFDA shows multiple fluorescent bands, indicating that CMFDA reacts indiscriminately with cell proteins carrying free thiols. Extracts of cells treated with 5-(pentachlorobenzoylamino)fluorescein diacetate show a single band in the region of the tracking dye apparently corresponding to the free dye and do not shown a protein adduct, either.

Alternatively, the above samples are analyzed by TLC and by HPLC, as described in Examples 48 and 52. TLC shows formation of a GSH adduct only in the cells treated with Compound 4 and 5-pentafluorobenzenesulfonylamino) fluorescein diacetate. Only a single, fast-moving fluorescent band corresponding to authentic 5-(pentachlorobenzoylamino)fluorescein (Compound 48) is visible in the sample treated with 5-(pentachlorobenzoylamino)fluorescein diacetate. In addition to a nonmigrating spot at the origin, multiple TLC bands are observed in the sample treated with CMFDA, the major of which is the authentic glutathione adduct of 5-chloromethylfluorescein. The HPLC elution profile of the supernate of the cells treated with Compound 4 shows two peaks with elution times corresponding to the elution time of the two peaks of the GSH/GST/Compound 1 reaction performed in vitro as described in Example 45. Coinjection with authentic Compound 1 confirms the identity of the substrate peak and coinjection with the authentic Compound 1-GSH adduct (Example 45) confirms the identify of the other fluorescent product. Analysis of the extract of cells loaded with CMFDA, shows the glutathione adduct and additional small peaks.

Example 68

Time-Course of Viral Transmission:

In order to track the progression of viral infection in cultured cells, cells are infected with virus and labeled with a well-retained marker dye such as 5-(pentafluorobenzoylamino)fluorescein diacetate (Compound 4, Example 3). Other cells are loaded with a dye that is lost rapidly (such as 5-benzoylaminofluorescein diacetate (Compound 5, Example 3) to partially mimic any adverse effects of dye loading. An experiment in which uninfected cells are labeled with the marker dye, and infected cells are not, serves as a control for the effect of dye loading on the cells.

Chinook salmon embryo (CHSE) cells are removed from culture dishes by trypsinization, washed once in growth medium, and resupended to a density of $10^6$ cells/mL in fresh complete medium containing 10% fetal bovine serum (FBS). The resulting cell suspension is divided into two equal portions and one suspension is inoculated with infectious hematopoietic necrosis virus (IHNV) at a multiplicity of infection (MOI) of 10 PFU/cell. After 30 minutes at room temperature the infected cells are washed 3× by centrifugation and resuspended in the original volume of medium. Both the uninfected and the infected cell suspensions are divided in half. Enough 5 mM Compound 4 in DMSO to yield 5 $\mu$M Compound 4 in the medium is added to one infected and one uninfected cell suspension. Enough 5 mM 5-benzoylaminofluorescein diacetate (Compound 5) in DMSO to yield 5 $\mu$M Compound 5 in the medium is added to one infected and one uninfected cell suspension. All suspensions are incubated in screw-capped polypropylene tubes on a rotator for 30 minutes at 15° C. All suspensions are then washed twice by gentle centrifugation and resuspended to their original volume in fresh complete growth medium. Equal volumes of suspensions containing infected, Compound 4-labeled cells and uninfected Compound 5-labeled cells, or uninfected Compound 4-labeled cells and infected Compound 5-labeled cells, are combined and 2 mL of mixture is added to each of five 35 mm culture dishes containing 22×22 mm glass No. 1 coverslips. The cells are placed in a 15° C. $CO_2$ incubator and removed after 3, 6, 12, 24 and 36 hours, fixed with 3.7% formaldehyde in phosphate-buffered saline (PBS) for 30 minutes, permeabilized with 0.2% Triton X-100 in PBS for 30 minutes, and rinsed in PBS. After blocking with 5% bovine serum albumin (BSA) in PBS for 30 minutes, rabbit polyclonal anti-IHNV coat protein IgG in 1% BSA is incubated with the cells for 30 minutes. The primary antibody is rinsed away and a TEXAS RED-conjugated goat anti-rabbit IgG (Molecular Probes, Inc.) antibody solution in 1% BSA is added and the sample is incubated for 30 minutes at room temperature. The staining solution is then rinsed away and the cells are washed with distilled water, air dried, and mounted by inverting over a drop of CYTOSEAL on a glass slide. The cell fluorescence is imaged with bandpass epifluorescence filters for fluorescein and TEXAS RED. Correlations between the PFB-fluorescein signal and TEXAS RED-labeled viral antigen are noted to establish whether previously uninfected cells contain viral antigen.

Example 69

Phagocytosis of Compound 4-labeled *E. coli*:

A culture containing approximately $10^9$ *Escherichia coli* per mL is pelleted at 10,000×g for 5 min and resuspended in E-pure water to an equivalent cell density. Compound 4 is added to a final concentration of 1 mM and the bacteria are exposed to several permeabilizing electrical pulses in a commercial electroporator. The cells are allowed to recover for 30 minutes at room temperature. Opsonizing IgG is then added to the bacterial suspension, which is incubated at 37° C. for 30 minutes, and subsequently the bacteria are washed by centrifugation into complete cell culture medium. Opsonized, fluorescently labeled bacteria are added to coverslip chambers containing previously-prepared adherent human neutrophils held at 37° C. Phagocytosis of fluorescent bacterial particles is monitored by wide-field epifluorescence microscopy using standard fluorescein optics.

It is to be understood that, while the foregoing invention has been described in detail by way of illustration and example, numerous modifications, substitutions, and alterations are possible without departing from the spirit and scope of the invention as described in the following claims.

What is claimed is:

1. A method of detecting glutathione in a sample, comprising:

a) preparing a solution comprising
      i) a sample that contains or is thought to contain glutathione;
      ii) a glutathione transferase; and
      iii) a glutathione transferase substrate of the formula

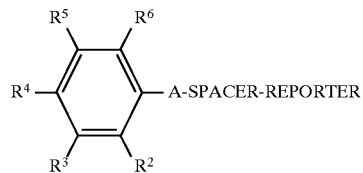

wherein
   $R^4$ is F;
   at least two of $R^3$, $R^5$ and $R^6$ are F; and the remaining of $R^3$, $R^5$ and $R^6$ are independently H, F, Cl, Br, $C_1$–$C_6$ alkyl, $C_1$–$C_6$ alkoxy;
   $R^2$ is H, F, Cl, Br, $C_1$–$C_6$ alkyl, $C_1$–$C_6$ alkoxy; or $R^2$ is $SO_3R^7$, (C=O)$OR^7$, or (C=O)$NR^8R^9$, where $R^7$ is H, a suitable counterion, or a $C_1$–$C_6$ alkyl, and $R^8$ and $R^9$ are independently H or a $C_1$–$C_6$ alkyl;
   A is —(C=O)—, —(C=O)—O—, —(C=O)—$NR^{10}$, —$NR^{10}$—(C=O)—, —(C=$NR^{10}$)—, —CH=N—, —$SO_2$—, —$SO_2$—O—, —$SO_2$— $NR^{10}$—, or —$NR^{10}$—$SO_2$—, where $R^{10}$ is H or $C_1$–$C_6$ alkyl;
   or $R^2$ in combination with A forms a 5-membered cyclic imide; or $R^2$ in combination with A forms a 6-membered cyclic succinic hydrazide;
   SPACER is a single covalent bond, or SPACER is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds;
   REPORTER is a covalently bound moiety that is H, or an organic residue having a definite molecular weight less than 2000 daltons; provided that all glutathione transferase substrates in the solution have the same chemical formula and the same isomeric configuration;

b) incubating the solution for a time sufficient to form a glutathione adduct of said substrate if glutathione is present in the sample;
   c) detecting the presence of said glutathione adduct.

2. A method, as claimed in claim 1, wherein REPORTER comprises a radioactive element, a spin label, or a dye moiety.

3. A method, as claimed in claim 2, wherein REPORTER is a dye moiety that is a chromophore, a chromogenic substrate, a fluorophore, a fluorogenic substrate, a phosphorescent dye, or a chemiluminescent precursor.

4. A method, as claimed in claim 3, wherein REPORTER is a pyrene, an anthracene, a naphthalene, an acridine, a stilbene, an indole or benzindole, an oxazole or benzoxazole, a thiazole, a benzothiazole, a 4-amino-7-nitrobenz-2-oxa-1,3-diazole, a cyanine, a porphyrin, a salicylate, an anthranilate, an azulene, a perylene, a pyridine, a quinoline, a coumarin, a 4-bora-3a,4a-diaza-s-indacene, a xanthene, an oxazine, a benzoxazine, a carbazine, a phenalenone or a benzphenalenone.

5. A method, as claimed in claim 3, wherein REPORTER is a fluorophore that is a carbazine, an oxazine, a coumarin, a xanthene, a naphthalene, a phenalenone, or a 4-bora-3a,4a-diaza-s-indacene.

6. A method, as claimed in claim 5, wherein REPORTER is a xanthene that is a fluorescein, a rhodol or a rhodamine.

7. A method, as claimed in claim 5, wherein REPORTER is a benzofluorescein, a dibenzofluorescein, a seminaphthofluorescein, a naphthofluorescein, a seminaphthorhodafluor, a resorufin, an aminooxazinone, or a diaminooxazine.

8. A method, as claimed in claim 3, wherein REPORTER is a fluorogenic substrate that has the formula FLUOR-BLOCK, wherein FLUOR is a fluorophore that is a xanthene, oxazine, carbazine or coumarin;

BLOCK is a monovalent moiety selected to be removable by action of an enzyme;

such that when FLUOR is no longer bound to BLOCK by a FLUOR-BLOCK bond, FLUOR has spectral properties different from those of said fluorogenic substrate.

9. A method, as claimed in claim 1, wherein A is —(C=O)—, —(C=O)—$NR^{10}$, or —$SO_2$—$NR^{10}$—.

10. A method, as claimed in claim 1, wherein each of $R^2$, $R^3$, $R^5$, and $R^6$ is F; A is —(C=O)—, —(C=O)—NH— or —$SO_2$—NH—; and REPORTER is a fluorescein, a rhodol, a rhodamine, a resorufin, or a coumarin.

11. A method, as claimed in claim 1, further comprising separating the glutathione adduct from said substrate.

12. A method, as claimed in claim 11, wherein said separating step is accomplished by solvent extraction, chromatography or electrophoresis.

13. A method, as claimed in claim 12, wherein said separating step is accomplished by thin layer chromatography, high performance liquid chromatography, column chromatography or paper chromatography.

14. A method, as claimed in claim 13, wherein said separating step is accomplished by gel electrophoresis, capillary zone electrophoresis, or paper electrophoresis.

15. A method, as claimed in claim 1, wherein the detecting step comprises detection using colorimetric absorption, fluorescence, phosphorescence, chemiluminescence, radioactivity, electron spin resonance, nuclear magnetic resonance, or mass spectroscopy.

16. A method, as claimed in claim 15, wherein the detecting step comprises detection of absorption or fluorescence.

17. A method, as claimed in claim 16, wherein the glutathione adduct has a visible fluorescence or chemiluminescence emission maximum beyond 425 nm.

18. A method, as claimed in claim 1, wherein the sample is a biological fluid.

19. A method, as claimed in claim 18, wherein the sample is a cell extract, or tissue homogenate.

20. A method of detecting glutathione transferase activity in a sample, comprising:
a) preparing a solution comprising
  i) a sample that possesses or is thought to possess glutathione transferase activity;
  ii) glutathione; and
  iii) a glutathione transferase substrate of the formula

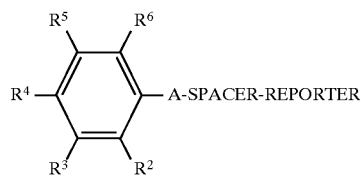

wherein
$R^4$ is F;
at least two of $R^3$, $R^5$ and $R^6$ are F; and the remaining of $R^3$, $R^5$ and $R^6$ are independently H, F, Cl, Br, $C_1$–$C_6$ alkyl, $C_1$–$C_6$ alkoxy;
$R^2$ is H, F, Cl, Br, $C_1$–$C_6$ alkyl, $C_1$–$C_6$ alkoxy; or $R^2$ is $SO_3R^7$, (C=O)$OR^7$, or (C=O)$NR^8R^9$, where $R^7$ is H, a suitable counterion, or a $C_1$–$C_6$ alkyl, and $R^8$ and $R^9$ are independently H or a $C_1$–$C_6$ alkyl;

A is —(C=O)—, —(C=O)—O—, —(C=O)—$NR^{10}$, —$NR^{10}$—(C=O)—, —(C=$NR^{10}$)—, —CH=N—, —$SO_2$—, —$SO_2$—O—, —$SO_2$—$NR^{10}$—, or —$NR^{10}$—$SO_2$—, where $R^{10}$ is H or $C_1$–C6 alkyl;

or $R^2$ in combination with A forms a 5-membered cyclic imide; or $R^2$ in combination with A forms a 6-membered cyclic succinic hydrazide;

SPACER is a single covalent bond, or SPACER is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds;

REPORTER is a covalently bound moiety that is H, or an organic residue having a definite molecular weight less than 2000 daltons; provided that all glutathione transferase substrates in the solution have the same chemical formula and the same isomeric configuration;

b) incubating the solution for a time sufficient to form a glutathione adduct of said substrate if the sample possesses glutathione transferase activity;

c) detecting the presence of said glutathione adduct.

21. A method, as claimed in claim 20, wherein REPORTER comprises a radioactive element, a spin label, or a dye moiety.

22. A method, as claimed in claim 21, wherein REPORTER is a dye moiety that is a chromophore, a chromogenic substrate, a fluorophore, a fluorogenic substrate, a phosphorescent dye, or a chemiluminescent precursor.

23. A method, as claimed in claim 22, wherein REPORTER is a pyrene, an anthracene, a naphthalene, an acridine, a stilbene, an indole or benzindole, an oxazole or benzoxazole, a thiazole, a benzothiazole, a 4-amino-7-nitrobenz-2-oxa-1,3-diazole, a cyanine, a porphyrin, a salicylate, an anthranilate, an azulene, a perylene, a pyridine, a quinoline, a coumarin, a 4-bora-3a,4a-diaza-s-indacene, a xanthene, an oxazine, a benzoxazine, a carbazine, a phenalenone or a benzphenalenone.

24. A method, as claimed in claim 22, wherein REPORTER is a fluorophore that is a carbazine, an oxazine, a coumarin, a xanthene, a naphthalene, a phenalenone, or a 4-bora-3a,4a-diaza-s-indacene.

25. A method, as claimed in claim 22, wherein REPORTER is a xanthene that is a fluorescein, a rhodol or a rhodamine.

26. A method, as claimed in claim 25, wherein REPORTER is a benzofluorescein, a dibenzofluorescein, a seminaphthofluorescein, a naphthofluorescein, a seminaphthorhodafluor, a resorufin, an aminooxazinone, or a diaminooxazine.

27. A method, as claimed in claim 22, wherein REPORTER is a fluorogenic substrate that has the formula FLUOR-BLOCK, wherein FLUOR is a fluorophore that is a xanthene, oxazine, carbazine or coumarin;

BLOCK is a monovalent moiety selected to be removable by action of an enzyme;

such that when FLUOR is no longer bound to BLOCK by a FLUOR-BLOCK bond, FLUOR has spectral properties different from those of said fluorogenic substrate.

28. A method, as claimed in claim 20, wherein each of $R^2$, $R^3$, $R^5$, and $R^6$ is F, and A is —(C=O)—, —(C=O)—$NR^{10}$, or —$SO_2$—$NR^{10}$—.

29. A method, as claimed in claim 20, further comprising separating the glutathione adduct from said substrate.

30. A method, as claimed in claim 29, wherein said separating step is accomplished by solvent extraction, chromatography or electrophoresis.

31. A method, as claimed in claim 30, wherein said separating step is accomplished by thin layer chromatography, high performance liquid chromatography, column chromatography, paper chromatography, gel electrophoresis, capillary zone electrophoresis, or paper electrophoresis.

32. A method, as claimed in claim 20, wherein the detecting step comprises detection using colorimetric absorption, fluorescence, phosphorescence, chemiluminescence, radioactivity, electron spin resonance, nuclear magnetic resonance, or mass spectroscopy.

33. A method, as claimed in claim 32, wherein the detecting step comprises detection of absorption or fluorescence.

34. A method, as claimed in claim 33, wherein the glutathione adduct has a visible fluorescence or chemiluminescence emission maximum beyond 425 nm.

35. A method, as claimed in claim 20, wherein the sample is a biological fluid.

36. A method, as claimed in claim 35, wherein the sample is a cell extract or tissue homogenate.

37. A method, as claimed in claim 20, wherein the glutathione transferase activity is due to expression of a portion of a fusion protein, or expression of a transfected or transformed gene.

38. A compound having the formula

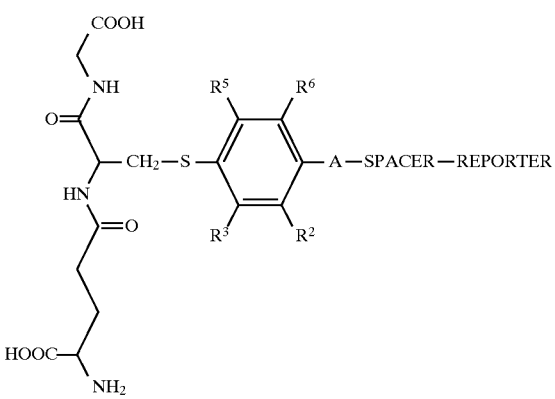

or the formula

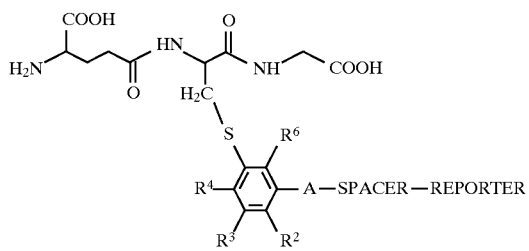

wherein $R^3$, $R^4$, $R^5$ and $R^6$ are independently H, F, Cl, Br, $C_1$–$C_6$ alkyl, $C_1$–$C_6$ alkoxy; provided that at least two of $R^3$, $R^4$, $R^5$, and $R^6$ are F;

$R^2$ is H, F, Cl, Br, $C_1$–$C_6$ alkyl, $C_1$–$C_6$ alkoxy; or $R^2$ is $SO_3R^7$, (C=O)$OR^7$, or (C=O)$NR^8R^9$, where $R^7$ is H, a suitable counterion, or a $C_1$–$C_6$ alkyl, and $R^8$ and $R^9$ are independently H or a $C_1$–$C_6$ alkyl;

A is —(C=O)—, —(C=O)—O—, —(C=O)—$NR^{10}$, —$NR^{10}$—(C=O)—, —(C=$NR^{10}$)—, —CH=N—, —$SO_2$—O—, —$SO_2$—$NR^{10}$—, or —$NR^{10}$—$SO_2$—, where $R^{10}$ is H or $C_1$–$C_6$ alkyl;

or $R^2$ in combination with A forms a 5-membered cyclic imide; or $R^2$ in combination with A forms a 6-membered cyclic succinic hydrazide;

SPACER is a single covalent bond, or SPACER is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds;

REPORTER is a covalently bound moiety that is H, or an organic residue having a definite molecular weight less than 2000 daltons.

39. A compound, as claimed in claim 38, wherein A is —(C=O)—, —(C=O)—$NR^{10}$, or —$SO_2$—$NR^{10}$—.

40. A compound, as claimed in claim 38, wherein REPORTER is a dye moiety that is a chromophore, a chromogenic substrate, a fluorophore, a fluorogenic substrate, a phosphorescent dye, or a chemiluminescent precursor.

41. A compound, as claimed in claim 40, wherein REPORTER is a pyrene, an anthracene, a naphthalene, an acridine, a stilbene, an indole or benzindole, an oxazole or benzoxazole, a thiazole, a benzothiazole, a 4-amino-7-nitrobenz-2-oxa-1,3-diazole, a cyanine, a porphyrin, a salicylate, an anthranilate, an azulene, a perylene, a pyridine, a quinoline, a coumarin, a 4-bora-3a,4a-diaza-s-indacene, a xanthene, an oxazine, a benzoxazine, a carbazine, a phenalenone or a benzphenalenone.

42. A compound, as claimed in claim 40, wherein REPORTER is a fluorophore that is a carbazine, an oxazine, a coumarin, a xanthene, a naphthalene, a phenalenone, or a 4-bora-3a,4a-diaza-s-indacene.

43. A compound, as claimed in claim 42, wherein REPORTER is a benzofluorescein, a dibenzofluorescein, a seminaphthofluorescein, a naphthofluorescein, a seminaphthorhodafluor, a resorufin, an aminooxazineone, or a diaminooxazine.

44. A compound, as claimed in claim 38, wherein each of $R^2$, $R^3$, $R^5$, and $R^6$ is F; and REPORTER is a fluorescein, a rhodol, a rhodamine, a resorufin, or a coumarin.

45. A compound having the formula

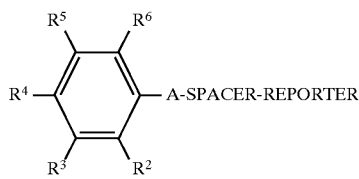

wherein $R^3$, $R^4$, $R^5$ and $R^6$ are independently H, F, Cl, Br, $C_1$–$C_6$ alkyl, $C_1$–$C_6$ alkoxy;

$R^2$ is H, F, Cl, Br, $C_1$–$C_6$ alkyl, C–$C_6$ alkoxy, $SO_3R^7$, (C=O)$OR^7$, or (C=O)$NR^8R^9$, where $R^7$ is H, a suitable counterion, or a $C_1$–$C_6$ alkyl, and $R^8$ and $R^9$ are independently H or a $C_1$–$C_6$ alkyl;

A is a single covalent bond, or A is —(C=O)—, —(C=O)—O—, —(C=O)—$NR^{10}$, —$NR^{10}$—(C=O)—, —(C=$NR^{10}$)—, —CH=N—, —$SO_2$—, —$SO_2$—O—, —$SO_2$—$NR^{10}$—, or —$NR^{10}$—$SO_2$—, where $R^{10}$ is H or $C_1$–$C_6$ alkyl;

or $R^2$ in combination with A forms a 5-membered cyclic imide; or $R^2$ in combination with A forms a 6-membered cyclic succinic hydrazide;

provided at least three of $R^2$, $R^3$, $R^4$, $R^5$ and $R^6$ are independently F, Cl or Br;

SPACER is a single covalent bond, or SPACER is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds;

REPORTER is a chromophore, a fluorophore, or a chemiluminescent precursor, or REPORTER has the formula DYE-(BLOCK)$_a$, wherein a=1 or 2; DYE is a chromophore, a fluorophore or a chemiluminescent precursor, and each BLOCK, which may be the same or different, is a monovalent moiety selected to be removable by action of an enzyme; such that when DYE is no longer bound to BLOCK by a DYE-BLOCK bond, DYE has spectral properties different from those of said compound;

provided that A and SPACER are not both single covalent bonds.

46. A compound, as claimed in claim 45, wherein REPORTER is a fluorophore that is a xanthene, oxazine, carbazine or coumarin.

47. A compound, as claimed in claim 45, wherein REPORTER is a benzofluorescein, a dibenzofluorescein, a seminaphthofluorescein, a naphthofluorescein, or a seminaphthorhodafluor.

48. A compound, as claimed in claim 45, wherein DYE is a fluorescein, a resorufin, a rhodamine or a rhodol, such that DYE, when bound to BLOCK is virtually nonfluorescent and when BLOCK is removed, DYE becomes fluorescent.

49. A compound, as claimed in claim 45, wherein each BLOCK is a monovalent moiety derived by removal of a hydroxy group from phosphate or from sulfate, or a biologically compatible salt thereof; or a monovalent moiety derived by removal of a hydroxy group from a carboxy group of an aliphatic or aromatic carboxylic acid or of an amino acid, protected amino acid, peptide, or protected peptide; or a monovalent moiety derived by removal of a hydroxy group from an alcohol or from a mono- or polysaccharide.

50. A compound, as claimed in claim 45, wherein each DYE-BLOCK bond is an amide bond resulting from removal of a hydroxy group from a carboxylic acid of an amino acid or peptide and a hydrogen atom from an amino moiety on DYE;

or an ether bond formed by removal of a hydroxy group from a $C_1$–$C_6$ alcohol or a mono- or polysaccharide and a hydrogen atom from a phenolic moiety on DYE;

or an ester bond formed by removal of a hydroxy group from an aliphatic or aromatic carboxylic acid and a hydrogen atom from a phenolic moiety on DYE.

51. A compound, as claimed in claim 45, wherein BLOCK is derived by removal of a hydroxy group from a $C_1$–$C_6$ alcohol or from a mono- or polysaccharide.

52. A compound, as claimed in claim 45, wherein DYE is a fluorescein, a rhodol, a resorufin or a coumarin; and each BLOCK is derived by removal of a hydroxy group from a glucose, a galactose, a glucuronic acid, a glucosamine, a galactosamine, a mannose, a xylose, a ribose or a fucose.

53. A compound, as claimed in claim 52, wherein each BLOCK is derived by removal of a hydroxy group from α-D-galactose, α-D-glucose, α-D-glucuronic acid, β-D-galactose, β-D-glucose or β-D-glucuronic acid.

54. A compound, as claimed in claim 45, wherein DYE is a fluorescein, a rhodol, a resorufin or a coumarin, and BLOCK is derived by removal of a hydroxy group from a phosphate.

55. A compound, as claimed in claim 45, wherein each of $R^2$, $R^3$, $R^4$, $R^5$ and $R^6$ is F or Cl; and A is —(C=O)—, —(C=O)—$NR^{10}$, or —$SO_2$—$NR^{10}$—.

56. A compound, as claimed in claim 45, wherein each of $R^2$, $R^3$, $R^4$, $R^5$, and $R^6$ is F, and A is —(C=O)—NH— or —$SO_2$—NH—.

57. A compound, as claimed in claim 45, wherein the fluorophore is a coumarin, such that the compound has the formula

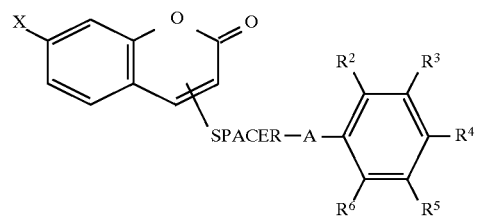

wherein

X is BLOCK—O—, BLOCK—$NR^{11}$—, HO— or $R^{11}R^{12}$N—, where $R^{11}$ and $R^{12}$ are independently H or $C_1$–$C_6$ alkyl; or $R^{11}$ and $R^{12}$ taken in combination form a pyrrolidine, a piperidine, a morpholine or a piperazine; or one or both of $R^{11}$ and $R^{12}$ in combination with the coumarin position ortho to X form a 5- or 6-membered saturated or unsaturated ring that is optionally substituted one or more times by methyl; and the coumarin is optionally substituted by H, halogen, sulfo, $C_1$–$C_6$ alkyl, $C_1$–$C_6$ perfluoroalkyl, $C_1$–$C_6$ alkoxy, cyano or halomethyl in any combination.

58. A compound, as claimed in claim 57, wherein X has the formula BLOCK—O— and BLOCK is derived by removing a hydroxy group from a from a $C_1$–$C_6$ alcohol or from a mono- or polysaccharide.

59. A compound, as claimed in claim 57, wherein X has the formula BLOCK—$NR^{11}$—, and BLOCK is derived by removal of a hydroxy group from a carboxylic acid of an amino acid or peptide.

60. A compound, as claimed in claim 45, wherein the fluorophore is a xanthene, such that the compound has the formula

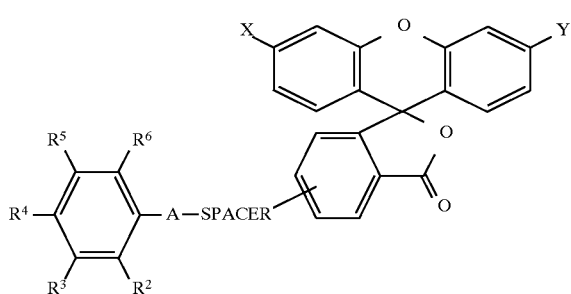

or the formula

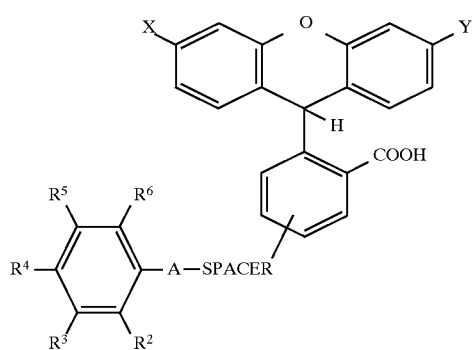

wherein

X and Y are independently BLOCK—O—, BLOCK—NR$^{11}$—, HO— or R$^{11}$R$^{12}$N—, where each R$^{11}$ and R$^{12}$ is independently H or C$_1$–C$_6$ alkyl; or R$^{11}$ and R$^{12}$ taken in combination form a pyrrolidine, a piperidine, a morpholine or a piperazine; or one or both of R$^{11}$ and R$^{12}$ in combination with a xanthene position ortho to X or Y form a 5- or 6-membered saturated or unsaturated ring that is optionally substituted one or more times by methyl; and the xanthene is optionally substituted by H, halogen, C$_1$–C$_6$ alkyl or C$_1$–C$_6$ alkoxy in any combination.

61. A compound, as claimed in claim 60, wherein X and Y are both BLOCK—NR$^{11}$—, and BLOCK is derived by removal of a hydroxy group from a carboxylic acid of an amino acid or peptide.

62. A compound, as claimed in claim 60, wherein X and Y are both BLOCK—O—, and BLOCK is derived by removal of a hydroxy from a glycoside, a carboxylic acid, a phosphate, or a sulfate.

63. A compound, as claimed in claim 62, wherein BLOCK is derived by removal of an anomeric hydroxy group from α-D-galactose, α-D-glucose, α-D-glucuronic acid, β-D-galactose, β-D-glucose or β-D-glucuronic acid.

64. A compound, as claimed in claim 62, wherein X and Y are both BLOCK—O—, and each BLOCK is acetate.

65. A compound, as claimed in claim 60, wherein each of R$^2$, R$^3$, R$^4$, R$^5$ and R$^6$ is F or Cl; and A is —(C=O)—, —(C=O)—NR$^{10}$, or —SO$_2$—NR$^{10}$—.

66. A compound, as claimed in claim 65, wherein each of R$^2$, R$^3$, R$^4$, R$^5$, and R$^6$ is F, and A is —(C=O)—NH— or —SO$_2$—NH—.

67. A compound, as claimed in claim 45, wherein the fluorophore is a xanthene, such that the compound has the formula

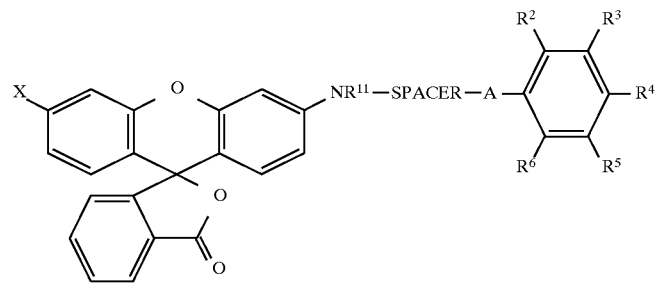

or the formula

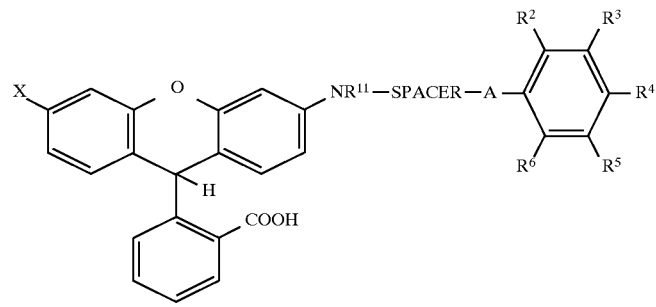

wherein

X is BLOCK—O, HO—, BLOCK—NR$^{11}$—, or R$^{11}$R$^{12}$N—, where each R$^{11}$ and R$^{12}$ is independently H or C$_1$–C$_6$ alkyl; or R$^{11}$ and R$^{12}$ taken in combination form a pyrrolidine, a piperidine, a morpholine or a piperazine; or one or both of R$^{11}$ and R$^{12}$ in combination with a xanthene position ortho to X form a 5- or 6-membered saturated or unsaturated ring that is optionally substituted one or more times by methyl; and the xanthene is further substituted by H, halogen, C$_1$–C$_6$ alkyl or C$_1$–C$_6$ alkoxy, in any combination.

68. A compound, as claimed in claim 67, wherein X is BLOCK—NR$^{11}$—, and BLOCK is derived by removal of a hydroxy group from a carboxylic acid of an amino acid or peptide.

69. A compound, as claimed in claim 67, wherein X is BLOCK—O—, and BLOCK is derived by removal of a hydroxy from a glycoside, a carboxylic acid, a phosphate, or a sulfate.

70. A compound, as claimed in claim 45, wherein the fluorophore is a resorufin, such that the compound has the formula

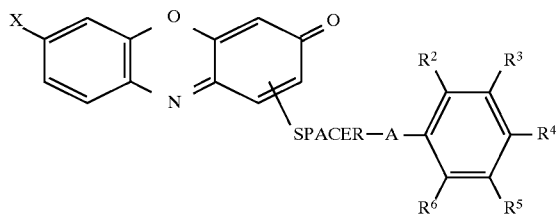

wherein

X is BLOCK—O—, or HO—; and the resorufin is further substituted by H, halogen, C$_1$–C$_6$ alkyl or C$_1$–C$_6$ alkoxy, in any combination.

71. A compound, as claimed in claim 70, wherein BLOCK is derived by removal of a hydroxy from a glycoside, a carboxylic acid, a phosphate, or a sulfate.

72. A compound, as claimed in claim 70, wherein BLOCK is derived by removal of an anomeric hydroxy group from α-D-galactose, α-D-glucose, α-D-glucuronic acid, β-D-galactose, β-D-glucose or β-D-glucuronic acid.

73. A method of analyzing enzyme activity in a sample, comprising a) preparing a solution comprising a compound of the formula

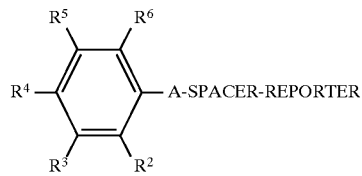

wherein

R$^3$, R$^4$, R$^5$ and R$^6$ are independently H, F, Cl, Br, C$_1$–C$_6$ alkyl, C$_1$–C$_6$ alkoxy;

R$^2$ is H, F, Cl, Br, C$_1$–C$_6$ alkyl, C$_1$–C$_6$ alkoxy; or R$^2$ is SO$_3$R$^7$, (C=O)OR$^7$, or (C=O)NR$^8$R$^9$, where R$^7$ is H, a suitable counterion, or a C$_1$–C$_6$ alkyl, and R$^8$ and R$^9$ are independently H or a C$_1$–C$_6$ alkyl;

A is a single covalent bond, or A is —(C=O)—, —(C=O)—O—, —(C=O)—NR$^{10}$, —NR$^{10}$—(C=O)—, —(C=NR$^{10}$)—, —CH=N—, —SO$_2$—O—, —SO$_2$—NR$^{10}$—, or —NR$^{10}$—SO$_2$—, where R$^{10}$ is H or C$_1$–C$_6$ alkyl;

or R$^2$ in combination with A forms a 5-membered cyclic imide; or R$^2$ in combination with A forms a 6-membered cyclic succinic hydrazide;

provided at least three of R$^2$, R$^3$, R$^4$, R$^5$ and R$^6$ are independently F, Cl or Br;

SPACER is a single covalent bond, or SPACER is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds;

REPORTER is a chromophore, a fluorophore, or a chemiluminescent precursor, or REPORTER has the formula DYE-(BLOCK)$_a$, wherein a=1 or 2; DYE is a chromophore, a fluorophore or a chemiluminescent precursor, and each BLOCK, which may be the same or different, is a monovalent moiety selected to be removable by action of an enzyme; such that when DYE is no longer bound to BLOCK by a DYE-BLOCK bond, DYE has spectral properties different from those of said compound;

provided that A and SPACER are not both single covalent bonds.

b) adding the solution to a sample that contains or is thought to contain an enzyme capable of cleaving at least one DYE-BLOCK bond and producing a detectable product;

c) incubating the sample for a time sufficient for the enzyme to cleave at least one DYE-BLOCK bond and produce said detectable product, d) observing the sample with means for detecting the detectable product;

e) correlating the presence of the detectable product with the enzyme activity.

74. A method, as claimed in claim 73, wherein the step of correlating further comprises quantitating the presence of the detectable product.

75. A method, as claimed in claim 73, wherein the step of observing comprising detecting fluorescence in the sample.

76. A method, as claimed in claim 73 wherein the enzyme is present within one or more cells.

77. A method, as claimed in claim 76, further comprising distinguishing cells in a sample based on the relative amounts of enzyme activity in the cells.

78. A method, as claimed in claim 77, wherein the cells are mammalian cells.

79. A method, as claimed in claim 73, wherein the enzyme is immobilized on a solid or semi-solid matrix or membrane.

80. A method, as claimed in claim 73, wherein DYE is a fluorescein, a resorufin, a rhodamine, or a rhodol such that DYE, when bound to BLOCK is virtually nonfluorescent and when each BLOCK is removed, DYE becomes fluorescent.

81. A method, as claimed in claim 73, wherein each BLOCK is a monovalent moiety derived by removal of a hydroxy group from phosphate or from sulfate, or a biologically compatible salt thereof; or a monovalent moiety derived by removal of a hydroxy group from a carboxy group of an aliphatic or aromatic carboxylic acid or of an amino acid, protected amino acid, peptide, or protected peptide; or a monovalent moiety derived by removal of a hydroxy group from an alcohol or from a mono- or polysaccharide.

82. A method, as claimed in claim 81, wherein the DYE-BLOCK bond is an amide bond resulting from removal of a hydroxy group from a carboxylic acid of an amino acid or peptide and a hydrogen atom from an amino moiety on DYE;

or an ether bond formed by removal of a hydroxy group from a $C_1$–$C_6$ alcohol or a mono- or polysaccharide and a hydrogen atom from a phenolic moiety on DYE;

or an ester bond formed by removal of a hydroxy group from an aliphatic or aromatic carboxylic acid and a hydrogen atom from a phenolic moiety on DYE.

83. A method, as claimed in claim 82, BLOCK is derived by removal of a hydroxy group from a $C_1$–$C_6$ alcohol or from a mono- or polysaccharide.

84. A method, as claimed in claim 73, wherein DYE is a fluorescein, rhodamine, rhodol, resorufin or a coumarin, and BLOCK is derived by removal of a hydroxy group from α-D-galactose, α-D-glucose, α-D-glucuronic acid, β-D-galactose, β-D-glucose or β-D-glucuronic acid.

85. A method, as claimed in claim 73, wherein each of $R^2$, $R^3$, $R^4$, $R^5$, and $R^6$ is F or Cl, and A is —(C=O)—, —(C=O)—$NR^{10}$, or —$SO_2$—$NR^{10}$—.

86. A method, as claimed in claim 85, wherein each of $R^2$, $R^3$, $R^4$, $R^5$, and $R^6$ is F, and A is —(C=O)—NH— or —$SO_2$—NH—.

* * * * *

UNITED STATES PATENT AND TRADEMARK OFFICE
CERTIFICATE OF CORRECTION

PATENT NO. : 5,773,236
DATED : June 30, 1998
INVENTOR(S) : Diwu, et al

It is certified that error appears in the above-identified patent and that said Letters Patent is hereby corrected as shown below:

On the title page, item [54] delete "ASSAY FOR GLUTATHIONE TRANSFERASE USING POLYHALOARYL-SUBSTITUTED REPORTER MOLECULES" and insert
-- POLYHALOARYL-SUBSTITUTED REPORTER MOLECULES FOR USE IN ENZYME ASSAYS--

Signed and Sealed this

Ninth Day of February, 1999

Attest:

Attesting Officer

*Acting Commissioner of Patents and Trademarks*

UNITED STATES PATENT AND TRADEMARK OFFICE
CERTIFICATE OF CORRECTION

PATENT NO.   : 5,773,236
DATED        : June 30, 1998
INVENTOR(S)  : Zhenjun Diwu and Richard P. Haugland It is certified that error appears in the above-identified patent and that said Letters Patent is hereby corrected as shown below:

Title page,
Item [73], Assignee, delete "Molecule Probes, Inc." and insert -- Molecular Probes, Inc. --.

Signed and Sealed this

Sixth Day of September, 2005

JON W. DUDAS
*Director of the United States Patent and Trademark Office*